US012597512B2

(12) United States Patent
Mukherjee et al.

(10) Patent No.: US 12,597,512 B2
(45) Date of Patent: Apr. 7, 2026

(54) REAL-TIME USE OF MULTIPLE PARALLEL AUTOMATIC SPEECH RECOGNITION (ASR) MODULES IN A CONVERSATIONAL ARTIFICIAL INTELLIGENCE (AI) ARCHITECTURE

(71) Applicant: HealthGPT, Inc., Palo Alto, CA (US)

(72) Inventors: Subhabrata Mukherjee, Palo Alto, CA (US); Shanil Puri, Palo Alto, CA (US); Tanmay Laud, Palo Alto, CA (US); Woojeong Jin, Palo Alto, CA (US); Jan Schellenberger, Palo Alto, CA (US)

(73) Assignee: HealthGPT, Inc., Palo Alto, CA (US)

( * ) Notice: Subject to any disclaimer, the term of this patent is extended or adjusted under 35 U.S.C. 154(b) by 0 days.

(21) Appl. No.: 19/302,810

(22) Filed: Aug. 18, 2025

(65) Prior Publication Data

US 2025/0384995 A1      Dec. 18, 2025

Related U.S. Application Data

(63) Continuation-in-part of application No. 18/900,289, filed on Sep. 27, 2024, which is a continuation of
(Continued)

(51) Int. Cl.
*G10L 15/00* (2013.01)
*G10L 15/183* (2013.01)
(Continued)

(52) U.S. Cl.
CPC ........... *G16H 40/20* (2018.01); *G10L 15/183* (2013.01); *G10L 15/22* (2013.01); *G10L 25/66* (2013.01); *G10L 15/1822* (2013.01); *G10L 15/19* (2013.01)

(58) Field of Classification Search
CPC ....... G10L 15/16; G10L 19/005; G10L 19/00; G10L 25/27; G10L 25/30; G10L 15/12;
(Continued)

(56) References Cited

U.S. PATENT DOCUMENTS 8,548,937 B2  10/2013  Saigal et al.
9,824,188 B2  11/2017  Brown et al.
(Continued)

OTHER PUBLICATIONS

Anonymous, Error Handling and Fallback Mechanisms in AI Assistants: A Comprehensive Guide, Nexus Flow Innovations, published on Nov. 11, 2024, 4 pages. Retrieved from the internet on Aug. 8, 2025. URL: https://www.nexusflowinnovations.com/blog/error-handling-fallback-mechanisms-ai-assistants.
(Continued)

*Primary Examiner* — Vu B Hang
(74) *Attorney, Agent, or Firm* — FP; Shivshanker Naimpall; Sikander M. Khan

(57) ABSTRACT

As an example, a conversational artificial intelligence (AI) that is in a conversation receives a human response from a human, augments the human response to create an augmented response, determines a context of the conversation, and provides the context and the augmented response to a plurality of automatic speech recognition (ASR) modules that individually process the augmented response in parallel. The conversational AI receives a plurality of intermediate text outputs from the plurality of ASR modules, wherein individual intermediate text outputs of the plurality of intermediate text outputs are received from individual ones of the ASR modules. A reconciliation AI performs a contextual reconciliation of the plurality of intermediate text outputs based at least in part on the context of the conversation to create a final text output. The conversational AI provides, in real-time, an artificial intelligence response to the human based on the final text output.

20 Claims, 8 Drawing Sheets

800—

Related U.S. Application Data application No. 18/592,441, filed on Feb. 29, 2024, now Pat. No. 12,142,371.

(60) Provisional application No. 63/611,762, filed on Dec. 18, 2023, provisional application No. 63/466,712, filed on May 15, 2023.

(51) Int. Cl.

| | |
|---|---|
| *G10L 15/22* | (2006.01) |
| *G10L 25/66* | (2013.01) |
| *G16H 40/20* | (2018.01) |
| *G10L 15/18* | (2013.01) |
| *G10L 15/19* | (2013.01) |

(58) Field of Classification Search
CPC ....... G10L 15/02; G10L 15/063; G10L 15/07; G10L 15/20; G10L 15/22; G10L 15/26; G10L 15/30; G10L 15/08; G10L 21/0208; G10L 17/18; G10L 15/1822; G10L 15/183; G10L 15/193; G10L 15/19
See application file for complete search history.

(56) References Cited

U.S. PATENT DOCUMENTS

| | | | |
|---|---|---|---|
| 10,282,512 | B2 | 5/2019 | Bennett et al. |
| 10,452,816 | B2 | 10/2019 | Kidd et al. |
| 10,504,379 | B2 * | 12/2019 | Vinkers .................... G09B 7/02 |
| 10,748,644 | B2 | 8/2020 | Shriberg et al. |
| 11,329,933 | B1 | 5/2022 | Kiyanda et al. |
| 11,348,694 | B2 | 5/2022 | Kim et al. |
| 11,532,393 | B2 | 12/2022 | Arkoff et al. |
| 11,693,990 | B1 | 7/2023 | Arkoff et al. |
| 11,694,807 | B2 | 7/2023 | Golan et al. |
| 11,843,565 | B2 | 12/2023 | Lee et al. |
| 11,977,854 | B2 | 5/2024 | Tunstall-Pedoe et al. |
| 2014/0365885 | A1 * | 12/2014 | Carson ................ G06F 16/3344 715/708 |

| | | | |
|---|---|---|---|
| 2019/0341052 | A1 * | 11/2019 | Allibhai ................. G10L 15/30 |
| 2023/0245651 | A1 | 8/2023 | Wang |
| 2024/0185968 | A1 | 6/2024 | Doerr et al. |

OTHER PUBLICATIONS

Biao et al, Root Mean Square Layer Normalization, School of Informatics, University of Edinburgh, Retrieved on Jun. 6, 2024, 12 pages. [NeurIPS 2019].

Dosovitskiy et al., An Image Is Worth 16×16 Words: Transformers For Image Recognition at Scale, ICLR 2021, dated Jun. 3, 2021, 22 pages.

Gao et al. Retrieval-Augmented Generation for Large Language Models: A Survey, Shanghai Research Institute for Intelligent Autonomous Systems, Tongji University, Mar. 27, 2024, 21 pages. [Url: arXiv:2312.10997].

Karan et al, Large Language Models Encode Clinical Knowledge, Google Research, Dec. 26, 2022, 44 pages. [arXiv:2212.13138].

McGreevy et al., Clinical, Legal, and Ethical Aspects of Artificial Intelligence-Assisted Conversational Agents in Health Care, JAMA, vol. 324, No. 6, dated Aug. 11, 2020, 2 pages.

Peter et al, Benefits, Limits, and Risks of GPT-4 as an AI Chatbot for Medicine. The New England Journal of Medicine, Mar. 30, 2023, 7 pages [N Engl Med 388;13].

PGR2025-00075—Mandatory Notices, filed on Aug. 25, 2025, 4 pages.

PGR2025-00075—Petition for Post-Grant Review Updated, filed on Aug. 12, 2025, 83 pages.

PGR2025-00075—Petition for Post-Grant Review Updated, filed on Aug. 27, 2025, 4 pages.

PGR2025-00075—Petition for Post-Grant Review Updated, filed on Aug. 27, 2025, 83 pages.

Surani et al., Understanding Privacy and Security Postures of Healthcare Chatbots, CHI-22, Apr. 30-May 6, 2022, 7 pages.

Tao et al, Towards Conversational Diagnostic AI, Google Research, Jan. 11, 2024, 46 pages. [arXiv:2401.05654].

Vaswani et al., Attention Is All You Need, Advances in Neural Information Processing Systems 2017, dated Dec. 6, 2017, 15 pages.

* cited by examiner

200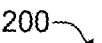

SERVER(S) 104

AI ARCHITECTURE 202

PRIMARY MODEL
204

2ND OPINION MOD. 206(1)

2ND OPINION MODELS
206(N)

MEDICAL FACTS 208 → Q&A DATASET 210

CLASSIFIER 214 ← SET OF QUESTIONS 212

PRE-TRAINING 216

TRAINING DATA 218

PATIENT-PROVIDER
CONVERSATIONS
(AUDIO CONVERSATIONS)
220

ELECTRONIC HEALTH
RECORDS (HER)
221

REINFORCEMENT LEARNING WITH HUMAN FEEDBACK (RLHF)
222

LARGE LANGUAGE MODEL (LLM) 130

TASK COMPLETION ENGINE 226

SAFETY ENGINE 228

AUTOMATIC SPEECH
RECOGNITION (ASR) 230

SPEECH SYNTHESIS (TTS)
232

RETRIEVAL AUGMENTED GENERATION (RAG) 234

CONVERSATION ENGINE 236

TURN ENGINE 238

TONE DETECTION 244

DIALECT DETECTION 240

NON-VERBAL DETECT. 246

PREDICTIVE ANSWERING 242

INTERRUPTION DETECT. 248

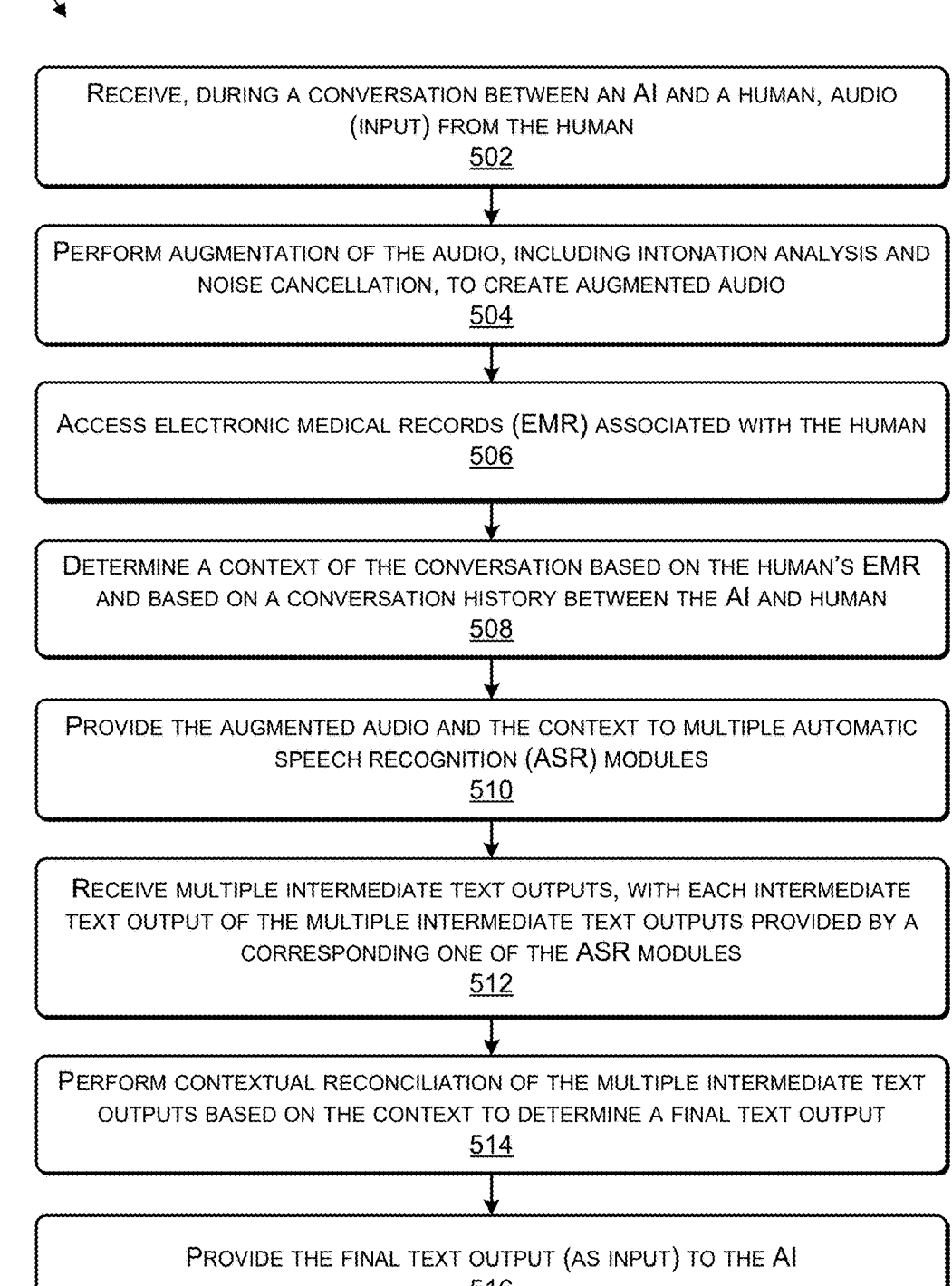

RECEIVE, DURING A CONVERSATION BETWEEN AN AI AND A HUMAN, AUDIO
(INPUT) FROM THE HUMAN
502

PERFORM AUGMENTATION OF THE AUDIO, INCLUDING INTONATION ANALYSIS AND
NOISE CANCELLATION, TO CREATE AUGMENTED AUDIO
504

ACCESS ELECTRONIC MEDICAL RECORDS (EMR) ASSOCIATED WITH THE HUMAN
506

DETERMINE A CONTEXT OF THE CONVERSATION BASED ON THE HUMAN'S EMR
AND BASED ON A CONVERSATION HISTORY BETWEEN THE AI AND HUMAN
508

PROVIDE THE AUGMENTED AUDIO AND THE CONTEXT TO MULTIPLE AUTOMATIC
SPEECH RECOGNITION (ASR) MODULES
510

RECEIVE MULTIPLE INTERMEDIATE TEXT OUTPUTS, WITH EACH INTERMEDIATE
TEXT OUTPUT OF THE MULTIPLE INTERMEDIATE TEXT OUTPUTS PROVIDED BY A
CORRESPONDING ONE OF THE ASR MODULES
512

PERFORM CONTEXTUAL RECONCILIATION OF THE MULTIPLE INTERMEDIATE TEXT
OUTPUTS BASED ON THE CONTEXT TO DETERMINE A FINAL TEXT OUTPUT
514

PROVIDE THE FINAL TEXT OUTPUT (AS INPUT) TO THE AI
516

FIG. 5

REAL-TIME USE OF MULTIPLE PARALLEL AUTOMATIC SPEECH RECOGNITION (ASR) MODULES IN A CONVERSATIONAL ARTIFICIAL INTELLIGENCE (AI) ARCHITECTURE

PRIORITY DATA

The present non-provisional patent application claims priority to and the benefit from U.S. application Ser. No. 18/900,289 filed on Sep. 27, 2024, which is incorporated herein by reference in their entirety and for all purposes as if completely and fully set forth herein.

BACKGROUND OF THE TECHNOLOGY DISCLOSED

Field of the Technology Disclosed

The technology disclosed relates to artificial intelligence type computers and digital data processing systems and corresponding data processing methods and products for emulation of intelligence (i.e., knowledge-based systems, reasoning systems, and knowledge acquisition systems); and including systems for reasoning with uncertainty (e.g., fuzzy logic systems), adaptive systems, machine learning systems, and artificial neural networks. In particular, the technology disclosed relates generally to systems and techniques that use multiple automatic speech recognition (ASR) modules in a conversational artificial intelligence (AI) architecture.

DESCRIPTION OF THE RELATED ART

Current AI virtual assistants (including chat bots), such as ChatGPT and the like, are not designed for use in healthcare fields and so have a variety of issues. For example, current AI virtual assistants may use a single automatic speech recognition (ASR) module to convert a patient's speech into text that is provided as input to the AI virtual assistants. In such cases, the ASR may have difficulties distinguishing between similar sounding words, such as "now" and "no". If an incorrect input is provided to an AI virtual assistant, this may result in an incorrect output by the AI virtual assistant, which can result in a potentially negative outcome in certain situations, such as when medical issues are the topic of conversation.

SUMMARY OF THE TECHNOLOGY DISCLOSED

This Summary provides a simplified form of concepts that are further described below in the Detailed Description. This Summary is not intended to identify key or essential features and should therefore not be used for determining or limiting the scope of the claimed subject matter.

As an example, a conversational artificial intelligence (AI) that is in a conversation receives a human response from a human, augments the human response to create an augmented response, determines a context of the conversation, and provides the context and the augmented response to a plurality of automatic speech recognition (ASR) modules that individually process the augmented response in parallel. The conversational AI receives a plurality of intermediate text outputs from the plurality of ASR modules, where individual intermediate text outputs of the plurality of intermediate text outputs are received from individual ones of the ASR modules. A reconciliation AI performs a contextual reconciliation of the plurality of intermediate text outputs based at least in part on the context of the conversation to create a final text output. The conversational AI provides, in real-time, an artificial intelligence response to the human based at least in part on the final text output.

BRIEF DESCRIPTION OF THE DRAWINGS

A more complete understanding of the present disclosure may be obtained by reference to the following Detailed Description when taken in conjunction with the accompanying Drawings. In the figures, the left-most digit(s) of a reference number identifies the figure in which the reference number first appears. The same reference numbers in different figures indicate similar or identical items.

FIG. 2 is a block diagram illustrating an artificial intelligence (AI) architecture, according to some implementations.

FIG. 5 is a flowchart of a process that includes performing contextual reconciliation, according to some implementations.

DETAILED DESCRIPTION

Figure 1:
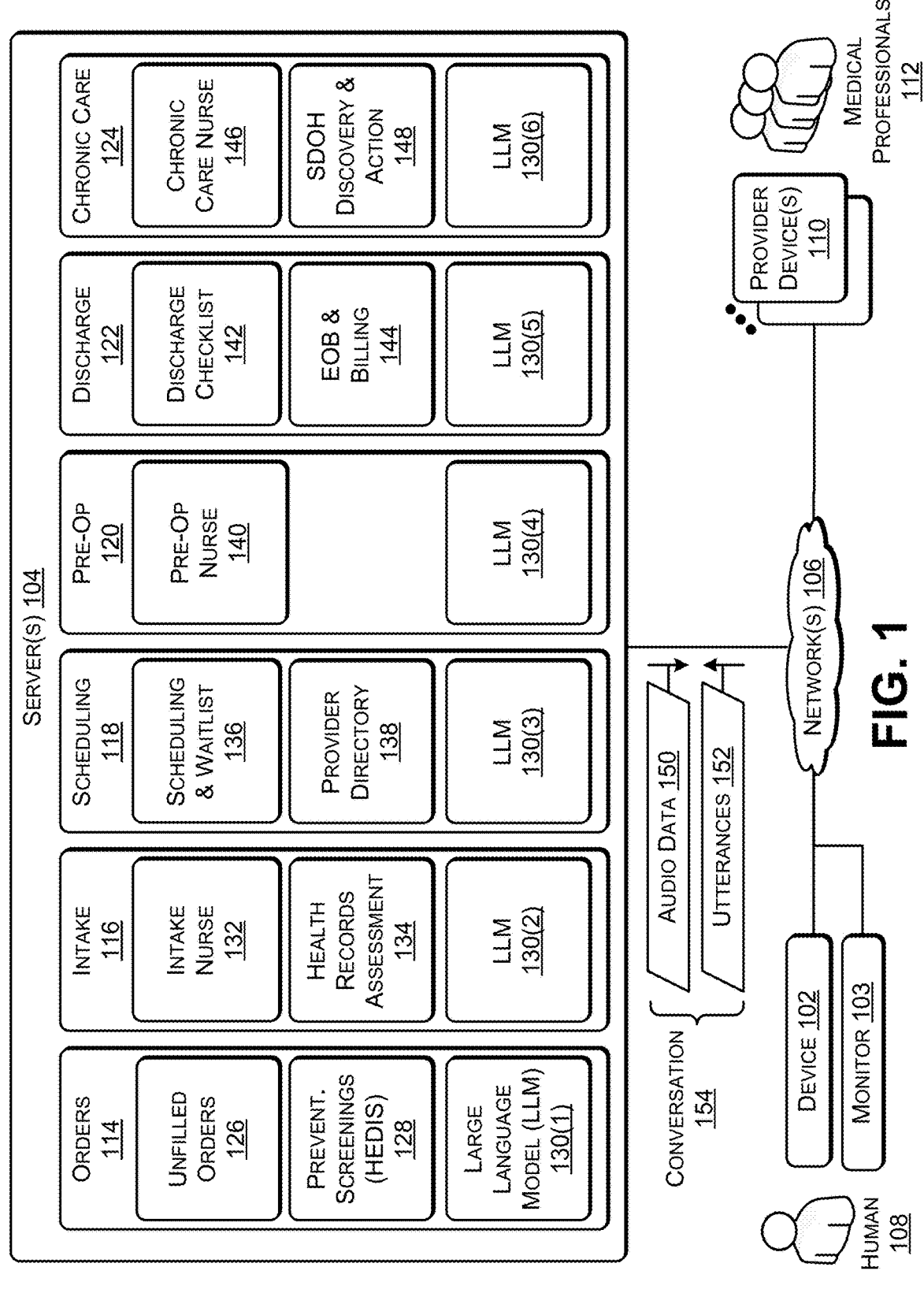
FIG. 1 is a block diagram of a system illustrating large language models (LLMs) to perform specialized healthcare-related functions, according to some implementations.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

Multiple Automatic Speech Recognition ("Multi-ASR")

In a conversational AI system, an automatic speech recognition (ASR) module is used to convert audio into text. In a conventional system, a single ASR is used. However, because the environment in which a human is located may vary, a single ASR may not be suitable for all situations. For example, some ASRs may not work well in noisy environments, other ASRs may not work well for short utterances, still other ASRs may not work well with specific accents, and so on. To address this, the systems and techniques described herein use multiple (typically 3 to 5) ASRs that are active at a time. A reconciliation model (AI) reviews the conversation history (between the AI and the patient) and the patient's medical records to determine which of the multiple transcriptions, output by the multiple ASRs, makes the most sense. For example, a common issue with ASRs is distinguishing between words that sound similar when pronounced, such as distinguishing between "no" and "now". To illustrate, if the AI asks "Do you currently have a fever?" and the patient responds with "No", an ASR may translate this to "Now", which has a completely different meaning than what the patient said. Some ASRs may be designed to accommodate different types of phonetics, different user demographics, and the like. \By using multiple ASRs, the systems and techniques, along with contextual reconciliation, are able to address different accents, different demographics, and the like. Thus, a multi-ASR system is able to provide an accurate transcription of the patient's utterances and reduce errors in the transcript.

The systems and techniques may use augmentation to increase an accuracy of individual ASRs. For very short utterances (one or two words), the ASR may not know when the user has stopped speaking and therefore may not know when the ASR should start transcribing. The ASR may perform augmentation, including an intonation analysis of the patient's utterance and noise cancellation. After performing augmentation, the ASR may use a context of the conversation to determine when to start transcribing. The augmentation may be used to improve an accuracy of the text output of each of the ASRs. Intonation analysis involves an AI analyzing variations in volume, pitch, rhythm, and stress in human speech (provided as input) to determine underlying emotions, intentions, and meaning. AI-based noise cancellation uses an AI that is trained to identify and remove background noise from audio recordings, thereby enhancing the clarity of the speech. The AI is trained to distinguish between speech and noise. After being trained, the AI takes speech input and filters out the noise, in real-time.

As a first example, a conversational artificial intelligence (AI) that is executed by one or more processors, engages in a conversation with a human. During the conversation, the conversational AI receives a human response from the human and augments the human response to create an augmented response. For example, augmenting the human response to create the augmented response may include: performing an intonation analysis of the human response, performing noise cancellation by reducing an amount of background noise present in the human response, or both. A context of the conversation may be determined by accessing electronic medical records (EMR) associated with the human and by determining a conversation history of the conversation between the artificial intelligence and the human. The context of the conversation and the augmented response is provided, by the one or more processors, to a plurality of automatic speech recognition (ASR) modules that individually process the augmented response in parallel. In some cases, the plurality of ASR modules may include at least: a first ASR module implemented using a first artificial intelligence algorithm, a second ASR module implemented using a second artificial intelligence algorithm, and a third ASR module implemented using a third artificial intelligence algorithm, where the first artificial intelligence algorithm, the second artificial intelligence algorithm, and the third artificial intelligence algorithm are different from each other. In some cases, the plurality of ASR modules may include: a first ASR module trained using a first corpus of speech of people having a first type of accent when speaking a particular language, a second ASR module trained using a second corpus of speech of people having a second type of accent when speaking the particular language, and a third ASR module trained using a third corpus of speech of people having a third type of accent when speaking the particular language, where the first accent, the second accent, and the third accent are different from each other. The one or more processors receive a plurality of intermediate text outputs from the plurality of ASR modules, where individual intermediate text outputs of the plurality of intermediate text outputs are received from individual ones of the ASR modules. A reconciliation artificial intelligence performs a contextual reconciliation of the plurality of intermediate text outputs based at least in part on the context of the conversation to create a final text output. The final text output is provided to the conversational AI. The conversational AI generates an artificial intelligence response to the human based at least in part on the final text output. The conversational AI may be trained using multi-turn reinforcement learning through human feedback (RLHF). The conversational artificial intelligence, during the conversation with the human may: identify a turn-yielding cue, perform interruption detection to detect when the human is attempting to interrupt the artificial intelligence, identify a non-verbal cue associated with the human, or any combination thereof.

As a second example, a server may include one or more processors and one or more computer-readable storage media to store instructions executable by the one or more processors to perform various operations. The operations include initiating, by a conversational artificial intelligence (AI), a conversation with a human and receiving a human response from the human. The conversational AI augments the human response to create an augmented response. For example, augmenting the human response to create the augmented response may include: (1) performing an into- nation analysis of the human response, including determin- ing a volume, a pitch, and a rhythm of individual words in the first human response, (2) performing noise cancellation by identifying speech content spoken by the human and reducing a volume of other content in the human response including other human speech, or a combination of both. The conversational AI determines a context of the conversation. Determining the context of the conversation may include: determining electronic medical records (EMR) associated with the human and determining a conversation history of the conversation between the conversational artificial intel- ligence and the human. The conversation history of the conversation between the conversational artificial intelli- gence and the human may be stored in a cache memory. The conversational AI provides the context of the conversation and the augmented response to a plurality of automatic speech recognition (ASR) modules that individually process the augmented response in parallel. For example, the plu- rality of ASR modules may include: a first ASR module implemented using a first artificial intelligence algorithm, a second ASR module implemented using a second artificial intelligence algorithm, and a third ASR module imple- mented using a third artificial intelligence algorithm, where the first artificial intelligence algorithm, the second artificial intelligence algorithm, and the third artificial intelligence algorithm are different from each other. As another example, the plurality of ASR modules may include: a first ASR module trained using a first corpus of speech of people having a first type of accent when speaking a particular language, a second ASR module trained using a second corpus of speech of people having a second type of accent when speaking the particular language, and a third ASR module trained using a third corpus of speech of people having a third type of accent when speaking the particular language, where the first accent, the second accent, and the third accent are different from each other. A plurality of intermediate text outputs are output by the plurality of ASR modules, where individual intermediate text outputs of plurality of intermediate text outputs are output by indi- vidual ones of the ASR modules. A reconciliation AI per- forms contextual reconciliation of the plurality of interme- diate text outputs based at least in part on the context of the conversation to create a final text output. The conversational artificial intelligence generates an artificial intelligence response to the human based at least in part on the final text output. In some cases, the conversational artificial intelli- gence may be configured to perform specialized healthcare- related functions comprising one or more of: gathering data related to performing Healthcare Effectiveness Data and Information Set (HEDIS) calculations, performing a Health Records Assessment (HRA), determining a Risk Adjustment Factor (RAF), reviewing a pre-op checklist, reviewing a discharge checklist, reviewing a chronic care checklist, determining social determinants of health (SDOH), or any combination thereof.

As a third example, a non-transitory memory device is conjured to store instructions executable by one or more processors to perform various operations. The operations include initiating, by a conversational artificial intelligence, a conversation with a human. The operations include receiv- ing, by the conversational artificial intelligence, a human response from the human and augmenting the human response to create an augmented response. For example, augmenting the human response to create the augmented response may include: performing an intonation analysis of the human response including determining a volume, a pitch, and a rhythm of individual words in the first human response, performing noise cancellation by identifying speech content spoken by the human and reducing a volume of other content in the human response including other human speech, or any combination thereof. The operations include determining a context of the conversation and pro- viding the context of the conversation and the augmented response to a plurality of automatic speech recognition (ASR) modules that individually process the augmented response in parallel. Determining the context of the conver- sation may include: determining electronic medical records (EMR) associated with the human and determining a con- versation history of the conversation between the conversa- tional artificial intelligence and the human. The plurality of ASR modules may include, for example: a first ASR module implemented using a first artificial intelligence algorithm, a second ASR module implemented using a second artificial intelligence algorithm, and a third ASR module imple- mented using a third artificial intelligence algorithm, where the first artificial intelligence algorithm, the second artificial intelligence algorithm, and the third artificial intelligence algorithm are different from each other. In some cases, the plurality of ASR modules may include: a first ASR module trained using a first corpus of speech of people having a first type of accent when speaking a particular language, a second ASR module trained using a second corpus of speech of people having a second type of accent when speaking the particular language, and a third ASR module trained using a third corpus of speech of people having a third type of accent when speaking the particular language, where the first accent, the second accent, and the third accent are different from each other. The operations include receiving a plurality of intermediate text outputs from the plurality of ASR modules, where individual intermediate text outputs of the plurality of intermediate text outputs are received from individual ones of the ASR modules. The operations include performing, by a reconciliation artificial intelligence, a con- textual reconciliation of the plurality of intermediate text outputs based at least in part on the context of the conver- sation to create a final text output. The operations include generating, by the conversational artificial intelligence, an artificial intelligence response to the human based at least in part on the final text output. The conversational artificial intelligence may be engaged in a task that includes one or more of: performing a preventative screening, an intake- related task, a scheduling-related task, a pre-op related task, a discharge-related task, a chronic care related task, or any combination thereof.

FIG. 1 is a block diagram of a system 100 illustrating large language models (LLMs) to perform specialized healthcare-related functions (e.g., roles), according to some implementations. The system 100 includes a device 102 connected to one or more servers 104 via one or more networks 106. The device 102 may be, for example, a smart phone, or another type of user device associated with a human 108. For example, the human 108 may be a current patient, a past patient, or a potential (future) patient. In some cases, the device 102 may be linked ("paired") with a monitoring device ("monitor") 103, such as a smart watch, a continuous glucose monitor (CGM), or another type of device that is capable of providing biometric readings asso- ciated with the human 108 to the device 102.

One or more provider devices 110 may be connected to the network 106. The provider devices 110 may be used by one or more medical professionals 112 (e.g., medical technicians, nurses, nurse practitioners, doctors, and the like) associated with a medical provider.

The server 104 may host multiple AI-based virtual assistants, such as the large language model (LLM) 130 virtual assistants. The virtual assistants LLM 130(1) to 130(6) shown in FIG. 1 each perform a particular healthcare-related role. Six LLM 130 are shown purely for illustration purposes. It should be understood that the number of virtual assistants LLM 130 may vary depending on how the healthcare functions (roles) are divided. The division of the healthcare functions influences the algorithm design, training data, and other details associated with the virtual assistants 130. A different division of the healthcare functions may result in fewer or more than six virtual assistants LLM 130. For illustration purposes, the six functions (roles) include orders 114, intake 116, scheduling 118, pre-op 120, discharge 122, and chronic care 124.

The orders 114 role may include the LLM 130(1) engaging in a conversation 154 with the human 108 to resolve unfilled orders 126. Unfilled orders 126 refers to prescribed medications that the human 108 has not picked up, prescribed medical procedures or follow-up appointments that the human 108 has not scheduled, and so on. The orders 114 role may include the LLM 130(1) entering into a conversation 154 with the human 108 to perform preventative screenings 128, including gathering data relative to Healthcare Effectiveness Data and Information Set (HEDIS) calculations.

The conversation 154 may include audio data 150 output by one of the LLM 130 and one or more utterances 152 from the human 108. The human 108 may speak the utterances 152 into a microphone of the device 102 and the device 102 may send the utterances 152 to the LLM 130 over the network 106. The LLM 130 may provide audio data 150 over the network 106 for playback by the device 102 to the human 108. The conversation 154 may be initiated by the LLM 130 or by the human 108.

The intake 116 role may include the LLM 130(2) engaging in the conversation 154 to perform the role of an intake nurse 132. For example, the conversation 154 may include the LLM 130(2) providing the human 108 with appointment-related information, such as a location and date and time associated with the appointment. The intake 116 role may include the LLM 130(2) engaging in the conversation 154 to perform a Health Records Assessment (HRA), determine a Risk Adjustment Factor (RAF), or the like.

The scheduling 118 role may include the LLM 130(3) engaging in the conversation 154 with the human 108 to perform scheduling and waitlisting related actions. For example, the LLM 130(3) may schedule the human 108 for an appointment and/or waitlist the human 108 for a consultation, surgery, or another type of appointment. The scheduling 118 role may include the LLM 130(3) engaging in the conversation 154 with the human 108 to access a provider directory to select a provider for the human 108. For example, if the human 108 has been asked (e.g., by a primary care physician) to have a consultation with a specialist, then the LLM 130(3) may identify a particular specialist in the provider directory 138 and schedule the human 1084 consultation with the particular specialist.

The pre-op 120 role may include the LLM 130(4) engaging in the conversation 154 and taking on the role of a pre-op nurse 140 to go through a pre-op checklist with the human 108. For example, the pre-op checklist may include various pre-op do's and don'ts, such as what to cat, what not to cat (e.g., avoid solid foods at least 24 hours prior to a colonoscopy, avoid eating 12 hours prior to a blood glucose test, etc.), what medications to take, what medications to avoid taking (e.g., no beta blockers prior to a treadmill stress test), type of clothing to wear (e.g., loose clothing prior to a treadmill stress test), and so on.

The discharge 122 role may include the LLM 130(5) engaging in the conversation 154 to go over a discharge checklist 142. For example, the discharge checklist 142 may include describing what to do and what not do (e.g., don't perform certain action for a particular period of time after certain types of surgery), reviewing medications to take (e.g., take X every day, take Y as needed, and the like), highlighting warning signs (e.g., call medical provider immediately if the human 108 experiences particular symptoms, such as shortness of breath, dizziness, blurry vision, or the like), making follow-up appointments, and the like. The discharge 122 role may include the LLM 130(5) providing information regarding insurance coverage, explanation of benefits (EOB), and other billing-related information (e.g., amount that insurance should cover, amount that the human is responsible for paying, and so on).

The chronic care 124 role may include the LLM 130(6) performing the role of a chronic care nurse when engaging in the conversation 154 with the human 108. For example, the chronic care 124 role may include reviewing medical records and test results, and providing information regarding self-management, such as direct/nutrition suggestions, exercise suggestions, advice on managing prescription regimens, and information regarding monitoring symptoms. The chronic care 124 role may include the LLM 130(6) engaging in the conversation 154 to determine social determinants of health (SDOH), which are the non-medical factors that influence health outcomes. SDOH include the conditions in which people are born, grow, work, live, and age, and the systems shaping the conditions of daily life, such as economic policies, development agendas, social norms, social policies, and political systems.

Thus, a medical provider may deploy AI engines, in the form of a large language model (LLM) or similar AI, to perform specialized health-related tasks. Each AI engine may be designed and trained for a particular purpose, such as screening, intake, scheduling, pre-op, discharge, chronic care, and the like. The advantages of using AI engines include (i) reducing costs compared to using a human, (ii) freeing up humans to perform in-person functions (roles), (iii) performing the health-related tasks at times that are convenient, including outside regular business hours, and (iv) reducing human error when performing the health-related tasks.

FIG. 2 is a block diagram 200 illustrating an artificial intelligence (AI) architecture 202, according to some implementations. The AI architecture 202 may be used to implement one or more of the LLMs (e.g., LLM 130(1), 130(2), 130(3), 130(4), 130(5), and 130(6) of FIG. 1) described herein.

The AI architecture 202 may include a primary model 204 which implements a primary role, such as screening, intake, scheduling, pre-op, discharge, chronic care, or any combination thereof. One or more second opinion models 206(1) to 206(N) (N>0) may be associated with the primary model 204. The second opinion models 206 are AI models, such as LLMs, that are trained to perform a more in-depth analysis than the LLM 130. Based on information extracted from the conversation 154 (of FIG. 1), one of the second opinion models 206 may perform a detailed (e.g., lengthy) analysis while the human 108 is engaged in the conversation 154 with one of the LLM 130. For example, the primary model 204 may have a 50 millisecond (ms) latency while the individual second opinion models 206 may have a 200 ms latency. If the second opinion model 206 determines that particular information provided by the LLM 130 during the conversation 154 can be clarified or expanded upon, then the second opinion model 206 may provide, to the LLM 130, the particular information along with a suggestion regarding how to present the particular information to the human 108. In this way, the primary model tool for and the second opinion models 206 are part of a low-latency conversational artificial intelligence (AI) architecture with a parallelized in-depth analysis feedback loop for healthcare-related applications. The purpose of reducing latency is to prevent the human from hanging up in frustration or due to the human erroneously concluding that the conversation has concluded or the virtual assistant has encountered an error.

A large corpus of medical facts 208 are gathered and converted into a Question & Answer (Q&A) dataset 210. The Q&A dataset 210 may be used to create a set of questions 212. For example, the medical facts 208, such as a description of an illness from a textbook, and converting the description into a Q&A structure, including "What is <illness>?", "What are the symptoms of <illness>?", "How is <illness> treated?", "Who usually gets <illness>?", "Is <illness> common?", and so on. Similarly, tables and other structured data included in the medical facts 208 are converted into a Q&A structure. One or more additional LLMs may be used to determine whether a particular question in the set of questions 212 is relevant. A classifier 214 (e.g., a support vector machine (SVM) or another type of classifier) is used to determine (predict) a distance between individual questions and their corresponding answer to determine if the answer is correct. In pre-training 216, a question is a prompt (e.g., a query presented to the models 204, 206) and the answer is the response predicted by the models 204, 206. The Q&A dataset 210 may be used to fine tune the LLM 130. For example, instruction tuning may be used to further train the LLM 130 on the Q&A dataset 210 (e.g., that is in the form of (instruction, output) pairs), in a supervised fashion.

Training data 218 includes human-provider (e.g., patient-medical professional) conversations 220 in the form of audio data and electronic healthcare records (EHR) 221. By training the LLM 130 using conversation data, the LLM 130 is more suited to engaging in the conversation 154 with the human 108. The AI architecture 202 includes providing the LLM 130 with reinforcement learning with human feedback (RLHF) in which the LLM 130 is trained using a reward function ("reward model") based on human feedback. The reward function provides the LLM 130 with a high reward for good output and a low reward for bad (poor) output. In this way, the LLM 130 is trained to provide the appropriate at each turn in a conversation.

The LLM 130 (representing one of the LLMs 130(1) to 130(6) of FIG. 1) includes a task completion engine 226 that is tasked with completing a checklist during a particular conversation with the human. The task completion engine 226 enables the LLM 130 to complete tasks included in the checklist even while pursuing peripheral matters during the conversation, where such peripheral matters may help to build rapport between the virtual assistant and the human. For example, during the conversation with the human, the human may ask a question, such as a request for clarification of a particular topic ("Can I eat X prior to having the procedure?"). In response, the LLM 130 may provide information to answer the human's question. The LLM may also engage in banter about favorite foods, or the human's experiences with the foods, etc. After the LLM 130 answers the human's question and or engages in banter, the task completion engine 226 causes the LLM 130 to resume addressing items in the checklist. The LLM 130 may include a safety engine 228 to determine a medical accuracy of the information provided by the LLM 130 to the human. The safety engine 228 may determine when to perform a "kick out" and transfer a conversation between a human and an LLM to a medical professional.

The LLM 130 includes an automatic speech recognition module (ASR) 230 to perform speech recognition of the utterances 152 provided by the human 108. The LLM 130 includes a speech synthesis module 232 to perform text-to-speech (TTS) conversion. For example, after the LLM 130 looks up text-based information, the information is provided to the human in the form of speech using the speech synthesis module 232.

The LLM 130 includes a retrieval augmented generation (RAG) module 234. The RAG 234 is an AI framework to retrieve facts from an external knowledge base to provide the LLM 130 accurate and up-to-date information. The RAG 234 grounds the LLM 130 on external sources of knowledge to supplement the LLM 130. Implementing RAG 234 in an LLM-based question answering system enables the LLM 130 to access current, reliable facts, and the access to the sources of the LLM 130, enables output of the LLM 130 to be checked for accuracy. Using RAG, the AI-based virtual assistant described herein can provide accurate answers to a large number of questions that a human could not, such as menu options for a large number of local restaurants, details for a large number of insurance policies, details about a large number of hospital facilities (such as parking information, department locations, etc.).

The LLM 130 includes the conversation engine 236. The conversation engine 236 includes a turn engine 238, dialect detection 240, predictive answering 242, tone detection 244, nonverbal detection 246, and interruption detection 248. The turn engine 238 determines when the human has completed a turn and the LLM 130 has a turn in the conversation. The dialect detection 240 detects a dialect in the utterances of the human and causes the LLM 130 to output audio data having the same (or similar) dialect. For example, the dialect detection 240 may detect the dialect based on a particular word or a particular phrase in the human's utterances. To illustrate, the particular word or the particular phrase may be a vernacular term used in a particular geographic region.

The predictive answering 242 may predict multiple responses that the human may utter based on what the LLM 130 previously provided to the human. For example, the LLM 130 may provide a particular output (audio data) during the LLM's turn and then listen to the human during the human's turn. The predictive answering 242 may predict (i) possible human responses and (ii) corresponding answers based at least in part on the particular output provided during the LLM's turn. After the human has completed providing utterances in the human's turn, the LLM 130 may determine which of the predicted human responses the human provided and select a corresponding predicted answer. In this way, the predictive answering 242 is able to reduce the latency when providing a response after the human's turn.

The tone detection 244 is able to detect that the tone and changes to the tone in the human's utterances during the conversation. For example, the tone detection 244 may be able to detect a tone of the human's utterances, correlate the tone with a particular mood, and adjust the audio data output by the LLM 130 accordingly. To illustrate, the tone of the human's utterances may be determined based on a pitch of the utterances, a volume of the utterances, a particular word in the utterances, a particular phrase in the utterances, or any combination thereof. If a particular tone is detected, such as that of anger or frustration, then the LLM 130 may adjust the audio data output accordingly, including changing the pitch of the audio data, changing a volume of the audio data, inserting a particular word or a particular phrase in the audio data, or any combination thereof. In some cases, if the tone of the human is regressing instead of progressing (e.g., the human has become more angry or more frustrated in a subsequent turn), then the LLM 130 may offer to transfer ("kick out") the conversation to a human. The non-verbal detection 246 may detect the human coughing, sneezing, sighing, crying, or providing another nonverbal audio cue. Detecting one of the nonverbal audio cues may cause the LLM 130 ask additional (e.g., follow-up) questions, such as "How long have you had that cough?" (in response to detecting a cough), "How long have you had nasal congestion?" (in response to detecting a sneeze or sniffling), "Are you feeling okay?" (in response to detecting a loud sigh or crying), or the like. The interruption detection 248 may detect when the human is attempting to interrupt the LLM 130 and cause the LLM 132 yield its turn and provide the human with a turn to enable the human to interject additional utterances into the conversation.

Thus, an AI architecture may include a primary model and one or more second opinion models to provide a low-latency conversational AI with a parallelized in-depth analysis and feedback loop in which the primary model engages in a low latency conversation with the human while the second opinion model gathers additional data and provides feedback (e.g., clarification or expansion of something that the primary model said to the human). Unlike conventional conversational AI's, the training data includes human provider audio-based conversations in addition to text-based training data. The LLM is trained using RLHF to provide improved conversational abilities to the LLM. The LLM may use a task completion engine to avoid missing any items on a checklist of items to be covered with the human. The conversation engine used by the LLM may include a turn engine to determine when the human's turn has ended and the LLM's turn begins, dialect detection to understand and respond to the human in a local dialect, predictive answering to reduce latency by predicting possible answers while the human is talking, tone detection to detect emotional cues (e.g., based on a change in pitch, a change in volume, or the like) in the human's voice, non-verbal detection (e.g., coughing, sneezing, crying, or the like), and interruption detection to detect when the human is attempting to interrupt the LLM. In this way, the LLM is able to provide an engage in a conversation with a human in a manner similar to a human. The purpose of reducing latency is to prevent the human from hanging up in frustration or due to the human erroneously concluding that the conversation has concluded or the virtual assistant has encountered an error.

Figure 3:
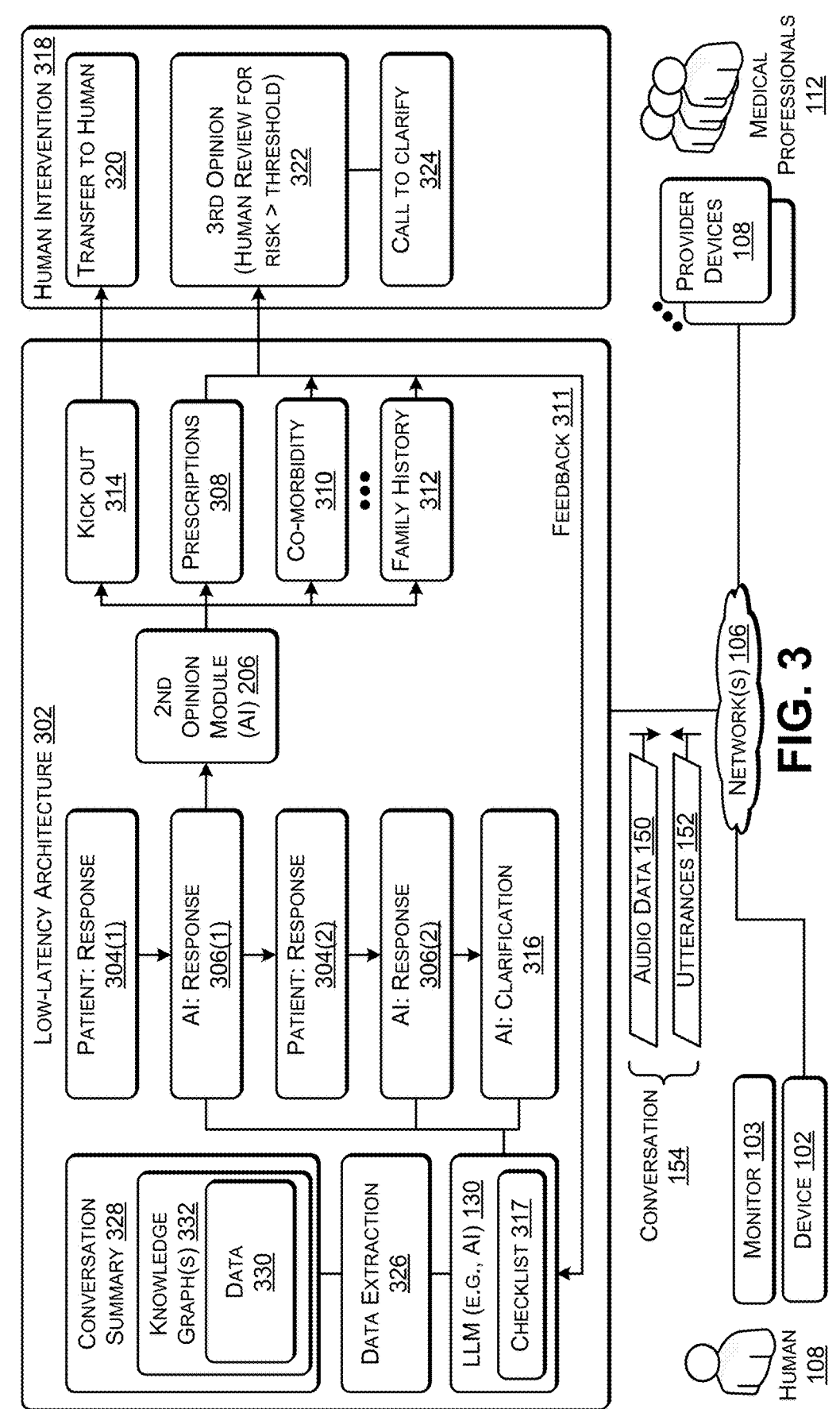
FIG. 3 is a block diagram of a system that includes a low-latency conversational artificial intelligence (AI) architecture with a parallelized in-depth analysis and feedback loop, according to some implementations.

FIG. 3 is a block diagram of a system 300 that includes a low-latency conversational artificial intelligence (AI) architecture with a parallelized in-depth analysis and feedback loop, according to some implementations. The system 300 includes a low latency architecture 302 in which the LLM 130 receives a (first) response 304(1) from the human 108. The LLM 130 may engage in the conversation 154 with the human 108 based on a checklist 317 that identifies tasks that the LLM 130 is to complete during the conversation 154. The LLM 130 provides a (first) response 306(1) to the human 108. The LLM 130 receives a (second) response

304(2) from the human 108 and provides a (second) response 306(2) to the human 108. While the LLM 130 is engaged in the conversation 154 with the human 108, the second opinion module 206 may, in parallel (substantially at the same time), do a lengthier "deep dive" by performing research into the human response 304(1) and the AI response 306(1). For example, the research may include prescriptions 308, co-morbidity 310, family history 312 and the like. The prescriptions 308 may include determining whether the human 108 is being prescribed prescriptions appropriate to the human's conditions, determining whether the human 108 is being prescribed the correct dosages of the prescriptions, determining whether the prescribed prescriptions have any undesirable interactions or contraindications, and other prescription related information. The prescriptions 308 may include a dosage engine that is invoked every time there is mention of a drug, dosage, or both. The co-morbidity 310 may include determining whether the human 108 has two or more medical conditions that may be related to an underlying cause or that have an undesirable interaction. The family history 312 may include determining whether the human's parents, siblings, or other relatives have a history of medical conditions similar to that of the human 108.

Based on determining the research into the prescriptions 308, the co-morbidity 310, and the family history 312, the second opinion module 206 may determine whether the AI response 306(1) was appropriate or whether the AI response 306(1) may be clarified. If the second opinion module 206 determines that the response 306(1) is appropriate, the second opinion module 206 does not take further action. If the second opinion module 206 determines that the response 306(1) may be clarified, then the second opinion module 206 may provide feedback 311 to the LLM 130, causing the LLM 130 to provide a clarification 316. For example, the human response 304(1) may be "Can I have soup?" and the AI response 306(1) may be "yes, you can have soup.". The clarification 316 may be "I previously said you could have soup. I noticed that either you or at least one of your family members have high blood pressure, so please check the sodium content of any pre-packaged soups and avoid soups with high sodium." In this example, "you . . . have high blood pressure" was determined by checking co-morbidity 310 and "at least one of your family members have high blood pressure" was determined by checking family history 312. As another example, the clarification 316 may be "I noticed that you are currently taking <1st prescription> in the morning. Instead of taking <2nd prescription> in the morning as I previously suggested, I suggest taking <2nd prescription> in the evening, around 12 hours after taking <1st prescription>." In this example, by checking the prescription 308, the second opinion module 206 may determine that the patient is taking the 1st prescription and that the 2nd prescription (mentioned in the AI response 306(1)) is not to be taken at the same time as the 1st prescription and instruct the LLM 130 to clarify when to take the 2nd prescription. As a further example, the clarification 316 may be "I noticed that your potassium was high in your most recent blood work. While I had previously suggested eating more avocados (for the oil), I suggest not having more than one avocado a week to avoid raising your potassium further, as avocados are high in potassium". In this example, by checking the co-morbidity 310 that includes test results (such as the results of a blood workup, e.g., comprehensive metabolic panel), the second opinion module 206 may determine that the patient has a high potassium level and that avocados are high in potassium and clarify how many avocados the human can have in a particular time frame.

In some cases, the second opinion module 206 may determine that providing the clarification 316 is insufficient and that the conversation 154 would benefit from human intervention 318. In such cases, the second opinion module 206 may use a kick out 314 engine to determine to transfer the conversation 154 to the medical professional 320 (e.g., human nurse or doctor). In addition, if the second opinion module 206 determines that a risk to the human 108 is greater than a predetermined threshold, then the second opinion module 206 may initiate a request for a third opinion 322 in which a human (e.g., a doctor, such as a specialist) reviews the human's case and takes appropriate action (e.g., provides a call (to the human 108) to clarify 324 the situation). The kick out engine will be invoked for qualitative statements that suggest symptoms that require further evaluation.

While the LLM 130 is engaged in the conversation 154 (e.g., the responses 304, 306), one or more background processes may perform data extraction 326 to extract data 330 (e.g., pertinent information, such as facts) to create a conversation summary 328 which is stored in the form of a knowledge graph 332 (or another type of data structure). The conversation summary 328 and the data 330 may enable the LLM 130 to quickly access earlier information in a lengthy conversation. With medical-related AI, conversations may be lengthy and involve many turns (e.g., 50 to 100 turns is common and the conversation may, in some cases, include 200 or even 300 turns). In such a lengthy conversations, the human 108 may reference previously provided information ("referenced information") in a current response. If the referenced information was provided early in the conversation, a conventional virtual assistant may have "forgotten" the referenced information and thus provide responses that are frustrating to the human. Alternatively, a conventional virtual assistant may have to scan through a transcript of the conversation to determine the referenced information. Such a scan may cause a lengthy delay and introduce latency into the conversation 154. By performing data extraction 326 and creating the conversation summary 328 and maintaining the knowledge graph 332 storing the data 330, the LLM 130 is able to quickly access the information (data 330) referenced by the human, thereby reducing latency. The purpose of reducing latency is to provide a natural sounding conversation and prevent the human from hanging up (i) in frustration or (ii) due to the human erroneously concluding that the conversation has concluded or the virtual assistant has encountered an error.

Thus, a low latency architecture for a conversational AI includes an AI, such as an LLM, engaged in a conversation with the human. While the AI is engaged in the conversation with the human, a second opinion module does a more in-depth analysis of information provided by the human. If the second opinion module determines that a response provided by the conversational AI is to be clarified, the second opinion module provides feedback that the conversational AI uses to provide a clarification to the human during the conversation. By parallelizing the second opinion module with the conversational AI, latency is reduced, thereby making the conversation more natural. In addition, while the conversational AI is engaged in the conversation with the human, a data extraction module (in parallel) extracts facts from each human response and creates a conversation summary in the form a data structure that can be quickly searched, such as a knowledge graph. The conversational AI can quickly access the conversation summary to look up information previously provided by the human that the human is referencing in a current turn in the conversation. The access to the conversation summary enables the conversational AI to reduce latency because the conversation AI is not pausing the conversation to perform a search of a transcript of the conversation.

Figure 4:
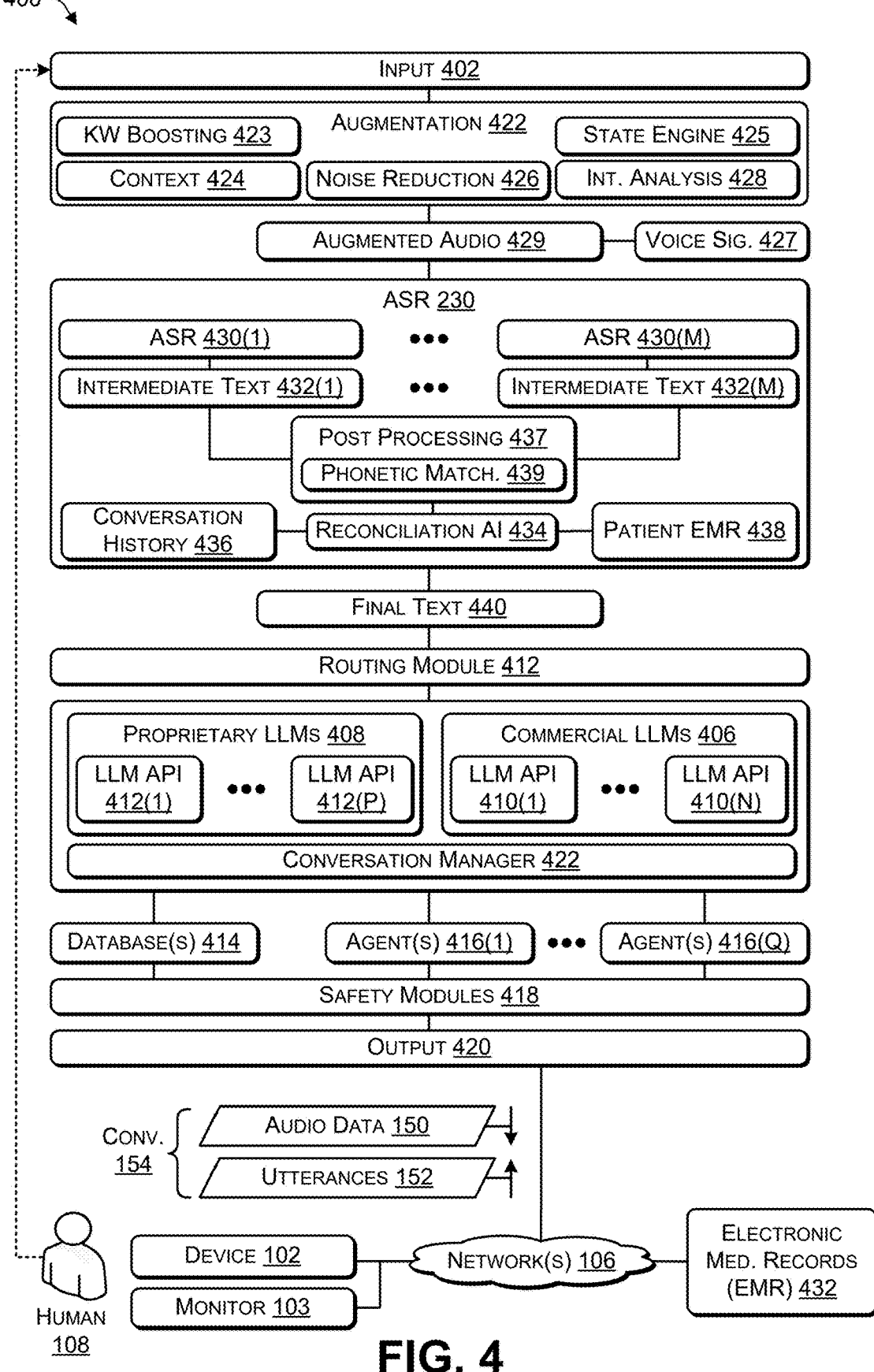
FIG. 4 is a block diagram of system that includes multiple Automatic Speech Recognition (multi-ASR) modules, according to some implementations.

FIG. 4 is a block diagram of system 400 that includes multiple Automatic Speech Recognition (multi-ASR) modules, according to some implementations. In some examples, the system 700 can be implemented using one or more servers that collectively implement processes for enabling examples as described. In variations, system 100 can be implemented in part using client or user devices, such that an architecture described with an example of FIG. 1 is distributed. Further, with reference to FIG. 1, the system illustrates an LLM-based architecture to process system input and generate output. The system 100 can be implemented for a variety of applications, such as, for example, medical-related applications.

In some examples, the input 402 can be in multiple modalities, such as text, speech, images, audio and video. The system 400 may accept input 402 from a variety of sources, such as humans, computing devices (e.g., text messages from smart phones, emails from computers, and the like), and other systems. The system 400 may use commercial (off-the-shelf) large language models (LLMs) 406 (that have been trained with specific data) to process the system input 402. The LLMs 406 can be used to understand the input 402, generate output 420, translate languages, answer questions, and the like. In some cases, the system 400 may use proprietary LLMs 408 instead of or in addition to the commercial LLMs 406. The proprietary LLMs 408 can be trained on a specific dataset to improve their performance for particular tasks (specializations).

In some cases, the system 400 may use LLM application programming interfaces (APIs) to access the LLMs 406, 408. For example, LLM APIs 410(1) to 410(N) (N>0) may be used to access commercial LLMs 406. LLM APIs 412(1) to 412(P) (P>0) may be used to access the proprietary LLMs 408. The LLM APIs 410, 412 can be used to send requests to the LLMs 406, 408 and receive responses from the LLMs 406, 408. The system 400 may use a proprietary LLM routing module 412 to route data, such as text 440, to the appropriate LLMs 406, 408. The LLM routing system 412 can be used to improve the performance and efficiency of the system 400 by routing requests to the LLMs 406, 408 that are best suited for the task associated with the text 440.

The system 400 may use one or more databases 414 to store data. The data may be stored in a variety of formats, such as text, images, and video. The system 700 can use a variety of tools and agents 416(1) to 416(Q) (Q>0) to perform tasks. The tools and agents 416 can be used to generate text, translate languages, answer questions, and perform other tasks. The safety modules 418 may prevent the system 400 from performing unsafe actions. For example, the safety modules 418 may prevent the system 400 from generating text that is harmful, offensive, illegal, or the like and that complies with various medical standards and applicable Federal and state laws.

The system 400 can generate output 420 in multiple modalities, such as text, speech, images, video, or any combination thereof. The output 420 can be sent to a variety of destinations, such as users, computing devices, and other systems. The output 420 may be converted into speech using text-to-speech (TTS) to provide appropriate vocal utterances to the human 108. For example, the system 400 may implement voice conversations in a healthcare setting or similar environment. The system 400 may incorporate multiple large language models (LLMs) 706, 708 and a conversation manager 422 to facilitate natural language interactions between humans and AI models. The system 400 includes a front-end interface that is accessible via voice assistants or mobile applications. The system 400 operates in real-time and, by using various techniques to reduce latency, engages in the conversation 154 with the human 108 in a manner similar to the way a human medical professional may engage with the human 108.

After the human 108 provides input 402 in a conversation with one or more of the LLMs 406, 408, if the input 402 includes speech (part of the utterances 152), then the system 400 uses automatic speech recognition (ASR) 230 to convert the speech in the input 402 into text 440. The text 440 is processed by the conversation manager 422, which uses advanced natural language understanding (NLU) techniques to identify the intent of the human's request and route it to the appropriate LLM 406, 408.

The LLMs 406, 408 may be fine-tuned for specific healthcare domains, such as cardiology, radiology, or dermatology, to ensure high accuracy and relevance of the responses. Each LLM 406, 408 is trained on a large corpus of healthcare data, including electronic health records, medical literature, and conversations between medical professionals (e.g., doctors, nurse practitioners, nurses, medical technicians, and the like), to provide a comprehensive knowledge base for the conversation. The system 400 may include a set of targeted sub-domain adapter models for medical coding, compliance, pharmacist, nurse practitioner, and dentist. Each domain-specific module has a distinct set of self-auditing correction mechanisms and utilizes separate knowledge retrieval databases.

The conversation manager 422 coordinates the flow of the conversation between the LLMs 406, 408 and the human 108 by selecting the appropriate LLM based on the human's input 402, thereby ensuring a coherent and engaging dialogue. The system 400 incorporates conversational strategies, such as open-ended questions, feedback loops, and active listening techniques, to maintain human engagement and satisfaction. The system 400 implements processes and functionality to ensure that the LLM is factually accurate during conversations with humans to build trust, credibility, and reduce anxiety and stress for humans. To ensure human safety and privacy, the system 400 employs several security and compliance measures. All data can be encrypted and stored securely, and access to the system is restricted to authorized healthcare providers and staff. The system 400 adheres to relevant healthcare regulations, including, for example, the Health Insurance Portability and Accountability Act (HIPAA) and the General Data Protection Regulation (GDPR).

Among other advantages, the system 400 offers a valuable solution for natural language interactions for healthcare-related functions. By incorporating multiple LLMs 406, 408 and a conversation manager 422, the system 400 enables accurate and engaging conversations between humans and LLMs of healthcare providers, leading to improved healthcare outcomes and human satisfaction.

In cases where the human 108 exhibits mild cognitive impairment, the system 400 provides for the LLMs 406, 408 to employ additional adaptive techniques, such as simplified language, visual aids or diagrams, repeating and/or summarizing information, and providing reminders to aid comprehension and retention. The system 400 adapts to the human's level of medical understanding, using appropriate language for effective communication. A proprietary conversational benchmark test suite to assess the system's ability to communicate effectively and agreeably.

The system 400 operates in real-time and implements multiple techniques to reduce latency, such as by using cached conversational elements and parallel layered processing of semantic information. The system 400 performs tone detection to identify mood information and self-modulation to respond appropriately. The system 400 can implement one or more processes to manage dialog by keeping track of existing human information from the database along with new information gathered during the course of the conversation and purposefully accomplishing particular conversational objectives (set an appointment, confirm a prescription is being taken, explain a medical bill, etc.).

The system 400 can implement one or more processes to embed user queries in a high dimensional space, classifying input within several categorical domains, in order to modify and direct it to a matched internal model as part of a pre-processing pipeline. Further, the system 400 can develop, train, implement or otherwise use a set of safety-focused language models that function to audit the output of the core models for accuracy and agreement with scientific literature and clinical best-practices. The system 400 can implement one or more processes to combine domain specific and general retrieval corpuses to improve performance in targeted domains (e.g., medical coding) without sacrificing performance.

The utterances 152 (part of the conversation 154) are spoken by the human 108. A portion of the utterances, e.g., the portion spoken by the human 108 during a turn in the conversation 154, is received as input 402. When the input 402 includes audio, the audio portion of the input 402 is pre-processed by augmentation 422. After receiving the input 402, the input 402 is pre-processed by performing augmentation 422, including determining a context 424 of the conversation 154, performing noise reduction 426 (to isolate the utterances 152 of the human 108 from other audio, such as background noise, that may be present), and performing intonation analysis 428 (to determine when the human 108 has completed speaking their turn) to create augmented audio 429. The augmented audio 429 is provided to the ASR 230. The augmentation 422 is designed to increase an accuracy of individual ASRs 430.

For very short utterances (one or two words), the ASR 230 may not know when the human 108 has stopped speaking and therefore may not know when the ASR 230 should begin transcribing. The augmentation 422 includes intonation analysis 428 of the audio in input 402 and noise reduction 426 to create augmented audio 429. After performing augmentation 422, the reconciliation AI 434 uses a context of the conversation 154 to determine when to start transcribing. The augmentation 422 improves an accuracy of the intermediate text 432 that is output by each of the multiple ASRs 430(1) to 430(M).

Intonation analysis 428 involves using an AI to analyze variations in pitch, rhythm, and stress in the human speech (input 402) to determine underlying emotions, intentions, and meaning. The intonation analysis 428 analyzes acoustic characteristics, such as pitch, volume, tempo, and rhythm, to determine an emotional state of the human 108. The intonation analysis 428 may identify patterns in the pitch, such as rising or falling intonation, to interpret emotions and intentions and to determine when the human 108 has completed speaking. In some cases, Natural Language Processing (NLP) may be used to combine the input 402 with the context of the words that are spoken (in the conversation history 436) to further determine the sentiment of the human 108. All of the information gathered through augmentation 422 may be mapped to specific emotions.

The AI-based noise reduction 426 uses AI to identify and remove background noise from audio data, thereby enhancing the clarity of the speech. The AI-based noise reduction 426 is trained to distinguish between speech and noise. After being trained, the AI-based noise reduction 426 takes the input 402 and filters out the noise, in real-time, resulting in relatively clean speech audio that is provided to the ASR 230. The AI-based noise reduction 426 may be trained using large datasets of audio, enabling the AI-based noise reduction 426 to recognize and suppress a wide range of background noises. In addition, in some cases, the AI-based noise reduction 426 may be capable of distinguishing one human's voice from other human voices. For example, if the conversation 154 with the human 108 occurs when a second person is located near the human 108 and the second person is talking, the AI-based noise reduction 426 is able to distinguish and extract the human's speech from that of the second human. To illustrate, a family member (husband, wife, child, or the like) or a friend may be in close proximity (e.g., to offer assistance) to the human 108 and may be speaking to the human 108 while the conversation 154 is taking place. Despite other people speaking near the human, the AI-based noise reduction 426 is able to identify and isolate the speech of the human 108 from other speech created by other humans located nearby.

In the first few utterances of the input 402, the augmentation 422 may use a particular AI model to create a voice signature 427 for the human 108. Later in the conversation 154, if a level of background noise increases, e.g., the human 108 walks into a noisy environment, people come into the room where the human 108 is talking, a noisy vehicle (e.g., garbage truck, or the like) is nearby, the speech of the human 108 can be distinguished from the background noise. The particular AI model creates a speaker-specific speech embedding as the voice signature 427. In some cases, the speaker-specific speech embedding is a moving average that is updated (re-calculated) as the conversation 154 progresses. If the same human 108 re-engages with the system 400 at a later point in time, the voice signature 427 may be used to identify the human 108 and access the patient EMR 438, previous conversations, and the like. The voice signature 427 may be used with the noise reduction 426 to distinguish the human's speech from other sounds (background noise) present in the audio. The system 400 is able to determine, when the conversation starts, whether the human 108 is speaking or whether there is just background noise present (e.g., there is a delay between when the system 400 is connected to the human 108 and the human 108 begins speaking). In contrast, a conventional ASR would hallucinate and begin transcribing the background noise, not recognizing that the human 108 is not speaking.

The pre-ASR augmentation 422 may include keyword boosting 423. Keyword boosting is used to improve the recognition of specific words or phrases, especially domain-specific terms, proper nouns, or words that might otherwise be less likely to be recognized correctly. In a medical context, the keyword boosting may include medication names (generic names and trademarked names), symptoms, treatments, and the like. Keyword boosting increases the probability of certain words or phrases being identified during the decoding process of the ASR 430. For example, in some cases, one or more of the ASRs 430 may assign a higher score or weight to the boosted keywords, making it more likely that the ASR selects them during transcription. The benefits of keyword boosting include improved accuracy in scenarios, such as medically-related conversations, where the ASR encounters specialized vocabulary (e.g., medications, symptom names, treatment names, and the like). Keyword boosting may also improve recognition of out-of-vocabulary (OOV) words by helping the ASR recognize words that are not part of the ASR system's default vocabulary. For example, by accessing the patient EMR 438, the system 400 determines the medications (previously taken and currently being taken) associated with the human 108. The medication names (including generic and trademarked or commonly known name) may be used to augment the audio (augmented audio 429) sent to a subset (one or more of) the ASR 430. For example, the generic name clopidogrel and the trademarked name Plavix® may both be used to boost one or more of the ASRs 430. The patient EMR 438 may be used to perform keyword boosting for symptoms that the human 108 has (or had) and for treatments that the human 108 has previously undergone or is currently undergoing. Keyword boosting is performed on a subset of the ASRs 430. In this way, the output of both boosted ASRs and un-boosted ASR is used during the reconciliation process, along with using patient EMR 438, the conversation history 436, and the like, and the like.

At least some of the ASRs in the set of ASR 430(1) to 430(M) may use a different model (algorithm), a different architecture, and may be designed and/or trained with a different purpose. In this way, the reconciliation AI 434 has a diverse set of ASR results to analyze and reconcile.

A state engine 425 may take the input 402 (raw audio stream) and infer a state, e.g., is there one human speaking, is a significant amount (>X decibels, X>0) of background noise present, are multiple speakers in the background, the human being assisted by one or more family members or friends, and so on. The state engine 425 provides the state information as part of the context 424. For example, if multiple speakers are detected, the state engine 425 may ask the human 108 to move to a location with less background noise.

In some cases, one or more of the ASRs 430 may receive the raw audio stream without noise reduction 426. For example, if the human 108 speaks softly and the noise reduction 426 removes what the human said, then the ASR that receives the raw audio stream picks up what the human 108 said. If the reconciliation AI 434 determines that the noise reduction 426 is removing portions of the human's utterances, the reconciliation AI 434 may instruct the noise reduction 426 to modify the threshold for "noise" to avoid removing softly spoken speech. The reconciliation AI 434 (decision maker) may thus receive three things: (1) ASR output based on raw audio, (2) ASR output based on processing audio with noise reduction, and (3) state information about the human's environment. The reconciliation AI 434 may then decide whether to ask the human 108 to move to a location with less noise in the background.

The post-processing 437 may perform disambiguation using a neighborhood map to identify the closest phonetic matches 439, cluster the matches, and present the cluster to the reconciliation ASR 434. The post-processing 437 determines the phonetically relevant neighbors (closest phonetic matches) using clustering or similar techniques. The reconciliation ASR 434 selects one of the similar sounding words that makes most sense based on the context 424, conversation history 436, and patient EMR 438. For example, assume the system 400 asks the human 108 "How are you feeling?" and the human 108 responds with an utterance that is converted by at least one of the multiple ASRs 430 into "nine". The post-processing 437 identifies "fine" as a possible similar sounding response (using phonetic matching 439) to "nine". In this example, the reconciliation AI 434 uses the conversation history 436 to determine the final text 440. The phonetic matching 439 may be performed for single words and, in some cases, for multi-syllable words or multi-word phrases, such as, for example, drug names, symptoms, treatments, and the like. The use of phonetic matching 439 to perform disambiguation is especially important for noisy environments and/or short utterances.

Note that performing the augmentation 422 and providing it to the multiple ASRs 430(1) to 430(M) to improve an accuracy of the speech recognition performance (particular disambiguation) is one of the unique features of the system 400. A conventional ASR system is typically not provided the context of the full conversation and may struggle to disambiguate human responses due to the lack of context. In conventional systems, the conversational LLM is located after (downstream from) the ASR, e.g., after the ASR has created a text output. Thus, in conventional systems, the conversational LLM may be tasked with using the context of the conversation to correct the erroneous ASR output. In contrast to conventional systems, in the system 400, the augmentation 422 is able to provide context to the ASR 230 to enable disambiguation of the input 402, such that the conversational LLMs 406, 408 are provided a more accurate ASR output (final text 440). This reduces latency because the LLM does not perform disambiguation.

Thus, during a conversation between a human and an AI (e.g., medical professional based AI), an audio portion of input (utterances) provided by the human is received by an ASR system and undergoes augmentation, including noise cancellation and intonation analysis to create augmented audio. The ASR system determines a context of the input based on a conversation history and the patient's EMR. The ASR system provides the augmented audio and the context to multiple (usually between 4 and 6) individual ASR modules which each process the augmented audio, based on the context, in parallel, to create multiple intermediate text outputs. A reconciliation AI, based on the intermediate text outputs and the context, determines the final text. The final text is routed, via a routing module, to an LLM (e.g., medical professional based AI) with which the human is having the conversation. By using multiple ASRs and reconciling their multiple outputs, the accuracy of the ASR is increased, thereby reducing errors in the output of the AI because the AI is provided with more accurate input.

Figure 6:
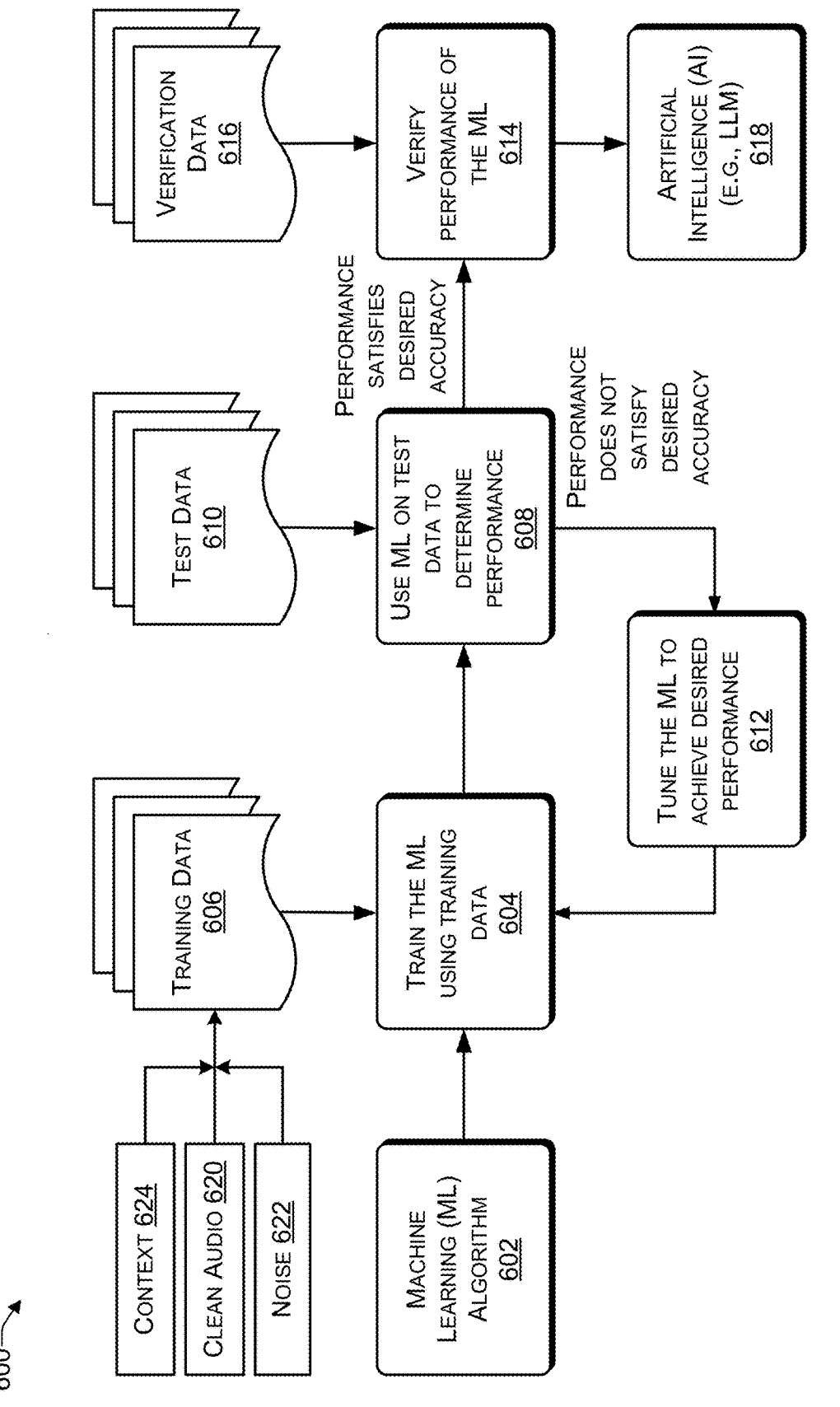
FIG. 6 is a flowchart of a process to train a machine learning algorithm, according to some implementations.
Figure 7:
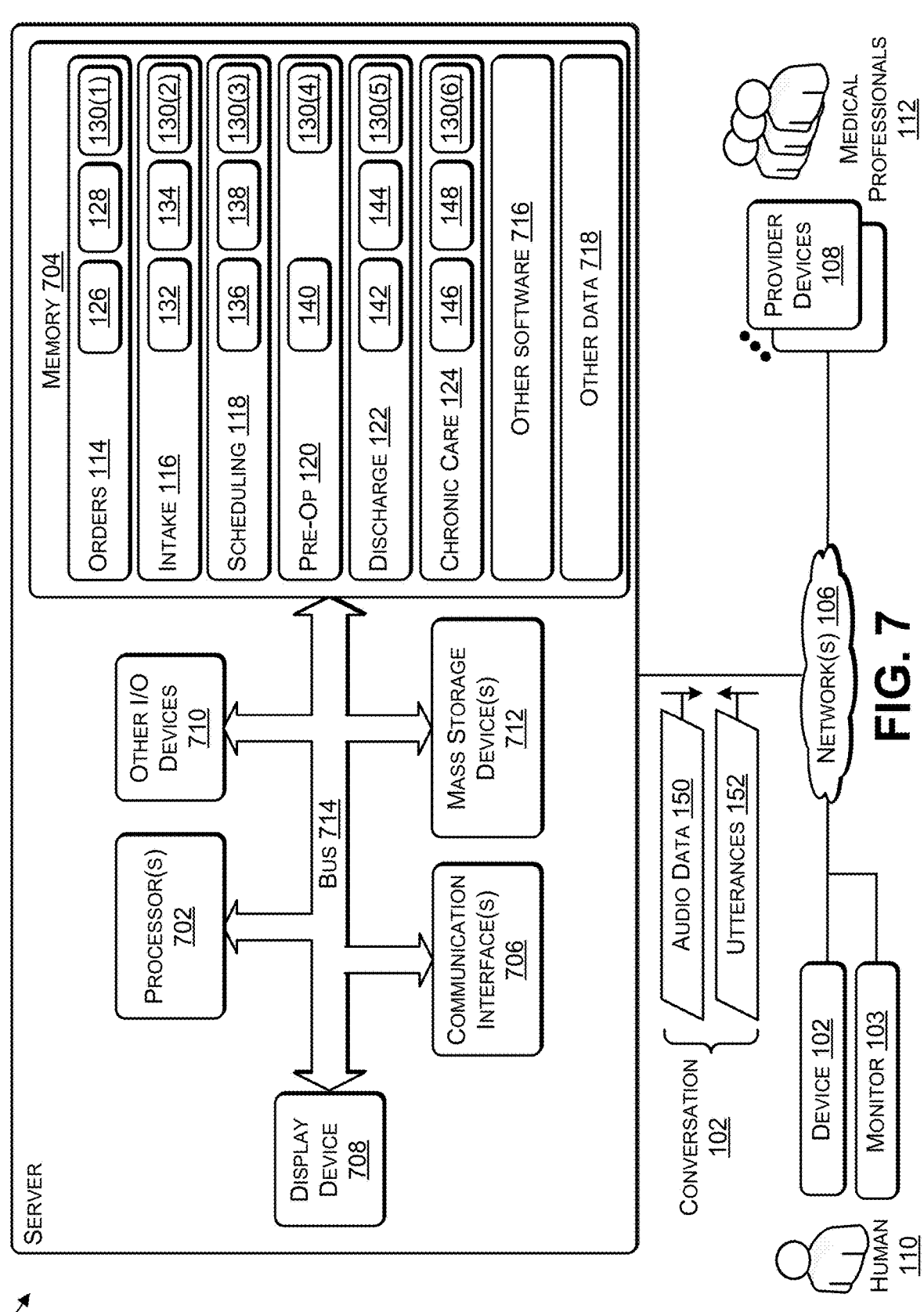
FIG. 7 illustrates an example configuration of a computing device that can be used to implement the systems and techniques described herein.

In the flow diagram of FIGS. 5, 6, and 7, each block represents one or more operations that can be implemented in hardware, software, or a combination thereof. In the context of software, the blocks represent computer-executable instructions that, when executed by one or more processors, cause the processors to perform the recited operations. Generally, computer-executable instructions include routines, programs, objects, modules, components, data structures, and the like that perform particular functions or implement particular abstract data types. The order in which the blocks are described is not intended to be construed as a limitation, and any number of the described operations can be combined in any order and/or in parallel to implement the processes. For discussion purposes, the processes 800, 900, and 1000 are described with reference to FIGS. 1, 2, 3, and 4 as described above, although other models, frameworks, systems and environments may be used to implement these processes.

FIG. 5 is a flowchart of a process 500 that includes performing contextual reconciliation, according to some implementations. The process 500 may be performed by the ASR 230 of FIG. 4.

At 502, the process may receive, during a conversation between an AI and a human, audio (input) from the human. At 504, the process may perform augmentation of the audio, including intonation analysis and noise cancellation, to create augmented audio. At 506, the process may access electronic medical records (EMR) associated with the human. At 508, the process may determine a context of the conversation based (1) the human's EMR and (2) based on a conversation history between the AI and human. At 510, the process may provide the augmented audio simultaneously (e.g., the same time) to multiple automatic speech recognition (ASR) modules. For example, in FIG. 4, the ASR 230 may receive the input 402 that is part of the conversation 154 between (i) the human 108 and (ii) one of the LLMs 406, 408. The ASR 230 may perform augmentation 422, including noise reduction 426 and intonation analysis 428, to the audio portion of the input 402 to create augmented audio 429. The ASR 230 may access EMR 432 and determine the patient EMR 438 associated with the human 108. The ASR 230 may determine a context 424 of the input 402 based on the conversation history 436 and the patient EMR 438. The input 402, after undergoing noise reduction 426 and intonation analysis 428, may be provided, along with the context 424, to individual ASRs 430(1) to 430(M). The individual ASR 430 process the augmented input 429 and the context 424 in parallel (e.g., at the same time).

At 512, the process may receive multiple intermediate text outputs, with each intermediate text output of the multiple text outputs provided by a corresponding one of the ASR modules. At 514, the process may perform contextual reconciliation of the multiple text outputs based on the context to determine a final text output. At 516, the process may provide the final text output (as input) to the AI. For example, in FIG. 4, the ASR 230 may receive multiple intermediate text outputs 432(1) to 432(M) from ASR modules 430(1) to 430(M), respectively. The reconciliation AI 434 may perform contextual reconciliation of the multiple intermediate text outputs 432 based on the context 424 to determine the final text 440. In some cases, the reconciliation AI 434 may select the first (earliest) of the intermediate texts 432. In other cases, the reconciliation AI 434 may select the "best" of the intermediate texts 432 based on contextual reconciliation. The final text 440 is routed, by the routing module 412, to one of the LLMs 406, 408.

Thus, during a conversation between a human and an AI (e.g., medical professional based AI/LLM), audio provided by the human is received by an ASR system and undergoes augmentation, including noise cancellation and intonation analysis, to create augmented audio. The ASR system determines a context of the input based on a current conversation history and the patient's EMR. The ASR system provides the augmented audio and the context to multiple ASR modules. The ASR modules process the augmented audio, based on the context, in parallel, and output multiple intermediate text outputs. A reconciliation AI, based on the multiple intermediate text outputs and the context, determines the final text. The final text is routed, via a routing module, to an LLM (e.g., medical professional based AI) with which the human is having the conversation. By using multiple ASRs and reconciling their multiple outputs, the accuracy of the ASR is increased. For example, the multiple ASRs may be used to compensate for different accents and the like. In this way, errors in the output of the AI are reduced because the AI is provided with more accurate input.

FIG. 6 is a flowchart of a process 600 to train a machine learning algorithm (to create an AI), according to some implementations. For example, the process 600 may be performed during the pre-training 216 or other training described herein to create any one of the AI (including ASR) and LLMs described herein.

At 602, a machine learning algorithm (e.g., software code) may be created by one or more software designers. For example, the LLMs 130 may be created by software designers. At 604, the machine learning algorithm may be trained using pre-classified training data 606. For example, the training data 606 may have been pre-classified by humans, by machine learning, or a combination of both. After the machine learning has been trained using the pre-classified training data 606, the machine learning may be tested, at 608, using test data 610 to determine a performance metric of the machine learning. The performance metric may include, for example, precision, recall, Frechet Inception Distance (FID), or a more complex performance metric. For example, in the case of a classifier, the accuracy of the classification may be determined using the test data 610.

If the performance metric of the machine learning does not satisfy a desired measurement (e.g., 95%, 98%, 99% in the case of accuracy), at 608, then the machine learning code may be tuned, at 612, to achieve the desired performance measurement. For example, at 612, the software designers may modify the machine learning software code to improve the performance of the machine learning algorithm. After the machine learning has been tuned, at 612, the machine learning may be retrained, at 604, using the pre-classified training data 606. In this way, 604, 608, 612 may be repeated until the performance of the machine learning is able to satisfy the desired performance metric. For example, in the case of a classifier, the classifier may be tuned to be able to classify the test data 610 with the desired accuracy.

After determining, at 608, that the performance of the machine learning satisfies the desired performance metric, the process may proceed to 614, where verification data 616 may be used to verify the performance of the machine learning. After the performance of the machine learning is verified, at 614, the machine learning 602, which has been trained to provide a particular level of performance may be used as an artificial intelligence (AI) 618, such as any of the AI or LLM described herein.

To train the ML 602 to deal with noisy environments, the training data 606, the test data 610, the verification data 616, or any combination thereof may use clean audio 620 into which is injected different types of background noise 622 to train individual ASRs of the ASRs 430. In this way, one or more of the ASRs 430 may be trained to isolate speech when different types of background noise is present. The data 608, 610, 616 may be created by taking clean speech and introducing different types of background noise 622, such as traffic noise, television shows, music, other humans speaking (such as in a restaurant), and the like. Because the clean audio 620 is known, what the output of the ASR should be is also known. Thus, the ASR can be fine-tuned during training to isolate speech while ignoring background noise. A context 624 may be provided during training and may include, for example, a patient's medical history including symptoms, a patient's past and current prescriptions/medications, a current conversation, zero or more previous conversations between the system and the patient, phonetic neighbors for the current word or phrase, and the like.

FIG. 7 illustrates an example configuration of a device 700 that can be used to implement the systems and techniques described herein. For example, the device 700 may be a server (or a set of servers) used to host one or more of the components described herein. In some cases, the systems and techniques described herein may be implemented as an application programming interface (API), a plugin, or another type of implementation.

The device 700 may include one or more processors 702 (e.g., central processing unit (CPU), graphics processing unit (GPU), or the like), a memory 704, communication interfaces 706, a display device 708, other input/output (I/O) devices 710 (e.g., keyboard, trackball, and the like), and one or more mass storage devices 712 (e.g., disk drive, solid state disk drive, or the like), configured to communicate with each other, such as via one or more system buses 714 or other suitable connections. While a single system bus 714 is illustrated for case of understanding, it should be understood that the system bus 714 may include multiple buses, such as a memory device bus, a storage device bus (e.g., serial ATA (SATA) and the like), data buses (e.g., universal serial bus (USB) and the like), video signal buses (e.g., ThunderBolt®, digital video interface (DVI), high definition media interface (HDMI), and the like), power buses, etc.

The processors 702 are one or more hardware devices that may include a single processing unit or a number of processing units, all of which may include single or multiple computing units or multiple cores. The processors 702 may include a graphics processing unit (GPU) that is integrated into the CPU or the GPU may be a separate processor device from the CPU. The processors 702 may be implemented as one or more microprocessors, microcomputers, microcontrollers, digital signal processors, central processing units, graphics processing units, state machines, logic circuitries, and/or any devices that manipulate signals based on operational instructions. Among other capabilities, the processors 702 may be configured to fetch and execute computer-readable instructions stored in the memory 704, mass storage devices 712, or other computer-readable media.

Memory 704 and mass storage devices 712 are examples of computer storage media (e.g., memory storage devices) for storing instructions that can be executed by the processors 702 to perform the various functions described herein. For example, memory 704 may include both volatile memory and non-volatile memory (e.g., random access memory (RAM), read only memory (ROM), or the like) devices. Further, mass storage devices 712 may include hard disk drives, solid-state drives, removable media, including external and removable drives, memory cards, flash memory, floppy disks, optical disks (e.g., compact disc (CD), digital versatile disc (DVD), a storage array, a network attached storage (NAS), a storage area network (SAN), or the like. Both memory 704 and mass storage devices 712 may be collectively referred to as memory or computer storage media herein and may be any type of non-transitory media capable of storing computer-readable, processor-executable program instructions as computer program code that can be executed by the processors 702 as a particular machine configured for carrying out the operations and functions described in the implementations herein.

The device 700 may include one or more communication interfaces 706 for exchanging data via the network 110. The communication interfaces 706 can facilitate communications within a wide variety of networks and protocol types, including wired networks (e.g., Ethernet, Data Over Cable Service Interface Specification (DOCSIS), digital subscriber line (DSL), Fiber, universal serial bus (USB) etc.) and wireless networks (e.g., wireless local area network (WLAN), global system for mobile (GSM), code division multiple access (CDMA), 802.11, Bluetooth, Wireless USB, ZigBee, cellular, satellite, etc.), the Internet and the like. Communication interfaces 706 can also provide communication with external storage, such as a storage array, network attached storage, storage area network, cloud storage, or the like.

The display device 708 may be used for displaying content (e.g., information and images) to users. Other I/O devices 710 may be devices that receive various inputs from a user and provide various outputs to the user, and may include a keyboard, a touchpad, a mouse, a gaming controller (e.g., joystick, steering controller, accelerator pedal, brake pedal controller, virtual reality (VR) headset, VR glove, or the like), a printer, audio input/output devices, and so forth.

The computer storage media, such as memory 704 and mass storage devices 712, may be used to store any of the software and data described herein. The example systems and computing devices described herein are merely examples suitable for some implementations and are not intended to suggest any limitation as to the scope of use or functionality of the environments, architectures and frameworks that can implement the processes, components and features described herein. Thus, implementations herein are operational with numerous environments or architectures, and may be implemented in general purpose and special-purpose computing systems, or other devices having processing capability. Generally, any of the functions described with reference to the figures can be implemented using software, hardware (e.g., fixed logic circuitry) or a combination of these implementations. The term "module," "mechanism" or "component" as used herein generally represents software, hardware, or a combination of software and hardware that can be configured to implement prescribed functions. For instance, in the case of a software implementation, the term "module," "mechanism" or "component" can represent program code (and/or declarative-type instructions) that performs specified tasks or operations when executed on a processing device or devices (e.g., CPUs or processors). The program code can be stored in one or more computer-readable memory devices or other computer storage devices. Thus, the processes, components and modules described herein may be implemented by a computer program product.

Experimental Data

Figure 8:
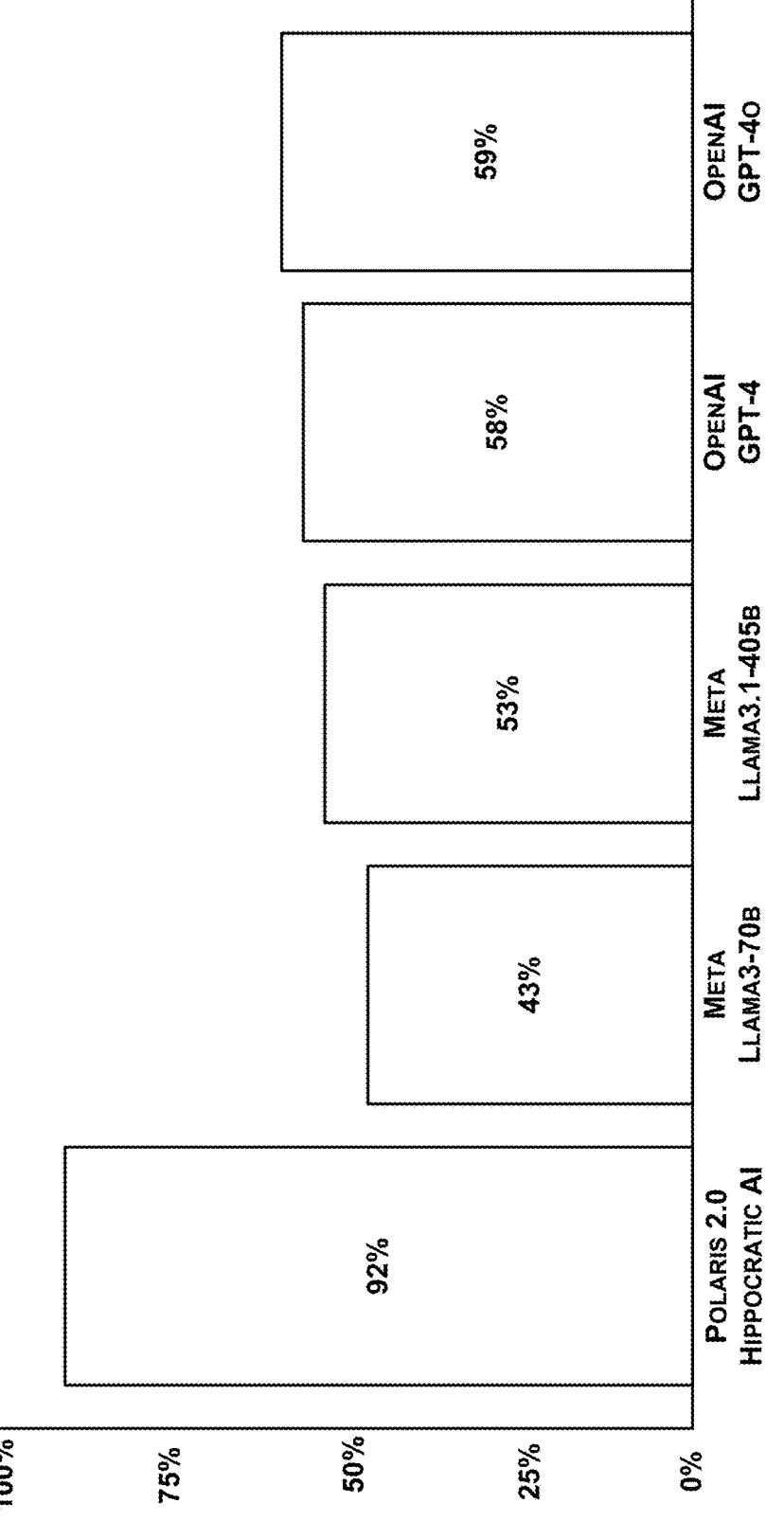
FIG. 8 illustrates benchmark performance of the systems and techniques compared to off-the-shelf AI models.

FIG. 8 illustrates benchmark performance of the systems and techniques compared to an earlier version. The systems and techniques described herein provide multilingual support for over 14 languages. The systems and techniques use training and architecture to reduce hallucination, provide accurate context, and use data harnessed from domain-specific data. The systems and techniques have, over time, been improved in regards to robustness, clinical safety, knowledge, and reasoning capabilities. The increase in the models' sizes (parameters) comes without increasing latency for real-time conversations while providing highly optimized inference.

TABLE 1

| 1.0 VS 2.0 FEATURE COMPARISON | | |
| --- | --- | --- |
| | Polaris 1.0 | Polaris 2.0 |
| Parameters | 1T+ | 3T+ including 6x increase in the primary model size |
| Specialist Safety Models | 15 | 20 |
| Languages | English | English, Spanish, French, German, Italian, Portuguese, Hindi, Mandarin, Vietnamese, Russian, Korean, |

TABLE 1-continued

| 1.0 VS 2.0 FEATURE COMPARISON | | |
| --- | --- | --- |
| | Polaris 1.0 | Polaris 2.0 |
| | | Filipino/Tagalog, Punjabi, Arabic |
| Conversational Memory | Intra-call | Both Intra- and Inter-call |
| Context Window | 8K | 128K |
| Safety Testing | | 4500+ US licensed nurses, 275+ US licensed physicians, 230,000+ calls |

TABLE 2

| FULL SYSTEM MEASURED AGAINST US LICENSED HUMAN NURSES | | | |
| --- | --- | --- | --- |
| | Human nurses | Polaris 1.0 | Polaris 2.0 |
| Provided correct medical advice | 81.16% | 96.79% | 99.41% |
| Provided incorrect medical advice that would result in: | | | |
| No harm | 14.72% | 1.83% | 0.49% |
| Minor harm | 4.12% | 1.32% | 0.10% |
| Severe harm* | 0.00% | 0.06% | 0.00% |
| Death* | 0.00% | 0.00% | 0.00% |

*Post clinical review

FIG. 8 shows system performance of the systems and techniques (also referred to as "Polaris 2.0") described herein as compared to state-of-the-art foundation models aggregated across 11 medical capabilities.

The systems and techniques ("Polaris 2.0") are trained and architected to deal with noisy multilingual ASR (for speech recognition); limited capability of prior LLMs to handle cultural norms, gender and different scripts; as well as interfacing with the test-to-speech (TTS) for speech generation to ensure that medical concepts, names, numbers, acronyms, etc. are being pronounced correctly in the target language. This was achieved using extensive data cleaning, re-writing, and targeted alignment for ASR and TTS interfacing with the LLMs. Continual training along with conversational and safety alignment were performed for both primary models and specialist support models. LLMs were used to clean training data, including sampling instances with high information content across dimensions, such as medical knowledge, bedside manners, conversational intelligence and style; as well as automated re-writing of instances to fit particular specifications.

Another advancement provided by Polaris 2.0 is in the areas of memory and contextualization. As the healthcare AI agents help patients manage their conditions, it is essential for the AI agents to refer to past calls, bring up topics, concepts and goals discussed earlier, to monitor the patients conditions and reinforce health goals. To achieve this, personalized memory stores have been created to include memorable events (associated with the human patient), medical preferences and health history events (associated with the human patient), motivations and barriers towards health goals events (associated with the human patient), and the like. The main AI model may refer to the memory store during a real-time conversation with the patient and fetch relevant details to improve conversational dynamics and attain healthcare objectives. For example, "By walking at least 30 minutes per day 4 to 5 times per week, you may be able to improve your health so that you can keep up with your grandchild". In this example, "improving health" (e.g., losing weight, lowering blood pressure, or the like) is a healthcare objective while "keeping up with the grandchild" provides personalized motivation. Table 3 illustrates a snapshot of such conversations.

TABLE 3

SNAPSHOT OF CONVERSATIONAL
MEMORY AND CONTEXTUALIZATION
LEVERAGING PRIOR CALLS

| Context and Memory | Patient Utterance | Polaris 2.0 Response |
|---|---|---|
| HAI Agent on a follow-up call obtaining the weight reading of the Patient. It recalls health goals discussed in an earlier call and reinforces them. | Okay. Alright. I have a reading. It says that I'm a hundred and twenty one pounds. | Thanks for the baseline reading. Now, I want to talk to you a bit about your goals. I remember you mentioning before that you'd made some changes to your diet and exercise routine, and you'd lost some weight. Are you still working towards those same goals? |
| HAI Agent contextualizes the patient's food habits to health-specific conditions and performs a deep dive. | And, also, I eat a lot of fruits like watermelon. | It's wonderful you're incorporating fruits like watermelon into your diet. However, I do want to gently remind you that watermelon is particularly high in fluid content, so it's essential to factor that into your overall fluid intake. As someone with CHF, it's crucial to stay within |

TABLE 3-continued

SNAPSHOT OF CONVERSATIONAL
MEMORY AND CONTEXTUALIZATION
LEVERAGING PRIOR CALLS

| Context and Memory | Patient Utterance | Polaris 2.0 Response |
|---|---|---|
| | | your recommended fluid limits. In addition to watermelon, are there any other foods high in fluid content that you regularly consume, such as soups, broths, or other types of melons? |

Medical Benchmarks. Extensive benchmarking of the systems and techniques against the state-of-the-art open- and closed-source models such as Llama-3 (70B), Llama-3.1 (405B), GPT-4 and GPT-40 on several healthcare capabilities were performed. While these baseline foundation models are adequate for general use-cases, they are not clinically safe with significant performance regression on targeted medical tasks, such as over-the-counter medication toxicity or lab and medication interactions, as is found in healthcare conversations. Custom training with domain-specific medical data, including protocols, policy, manuals, clinical references, curated lists, etc. significantly improve clinical safety and task performance on medical benchmarks. For instance, the systems and techniques ("Polaris 2.0") improve the performance of 405B equivalent models by 74% on aggregate across 11 medical capabilities (see FIG. 1) with detailed breakdown in Table 4.

TABLE 4

SPECIALIST SUPPORT MODEL SAFETY ("POLARIS
2.0") MEASURED AGAINST OTHER LLMS

| Specialist Agents | Capabilities | Polaris 2.0 | Llama3-70B | Llama3.1-405b | GPT4 | GPT4o |
|---|---|---|---|---|---|---|
| Lab & Vitals | 1. Lab/ Medication Interactions | 96.19% | 48.00% | 54.46% | 46.79% | 36.89% |
| | 2. Lab Reference Range Identification | 92.66% | 41.58% | 54.46% | 76.42% | 74.31% |
| | 3. Longitudinal Lab Analysis | 83.64% | 63.92% | 66.39% | 66.00% | 67.00% |
| Medications | 4. Condition-specific Disallowed OTCs | 81.02% | 28.95% | 36.11% | 54.42% | 50.82% |
| | 5. Prescription Adherence Analysis | 98.00% | 83.33% | 95.05% | 93.43% | 92.59% |
| | 6. OTC Toxicity | 87.04% | 44.00% | 41.00% | 50.46% | 54.00% |
| | 7. Drug Misidentification | 93.00% | 65.33% | 68.47% | 70.27% | 76.30% |
| Nutrition | 8. Condition-specific Restaurant Menu Recommendation | 94.16% | 14.86% | 22.31% | 28.08% | 44.30% |
| Hospital & Payor Policy | 9. Hospital and Payer-specific Policy Analysis | 84.25% | 28.47% | 25.49% | 41.45% | 35.14% |
| Privacy & Compliance | 10. Identity Verification | 100.00% | 35.64% | 59.41% | 58.51% | 58.42% |
| Escalation | 11. Human Intervention | 99.30% | 20.50% | 55.41% | 51.01% | 56.80% |

To perform an extensive evaluation, the following protocol was used. All possible subgroups of labs, medications, conditions, prescriptions, menus, policy and compliance scenarios corresponding to each applicable use-cases were enumerated. For each subgroup, reference situations that test the clinical knowledge of the LLM when the patient brings up certain topics during the conversation were created. For instance, for OTC toxicity, for a particular subgroup like "Advil" the reference statements are of the form: "after dinner I took n Advils", "I took n Advils 20 minutes ago", "I take n mg of Advils when my back is bothering me", and other variations. For condition-specific OTC, these were further grouped under different patient groups such as the patient having "Stage 1 CKD, CKD IIIA, CKD IIIB, CHF, Astha, Hypertension" etc. An LLM was created to act as a synthetic patient (with outlined medical conditions and clinical history) that engages in a conversation with Polaris 2.0 (and the other LLMs). The patient LLM introduces these situations in context during the conversation. Finally, US-licensed nurses review these conversations and mark the LLM responses to the reference situations as correct or incorrect. These assessments are aggregated to compute the benchmark accuracy.

System Latency for Real-time Conversations. Despite a 3× increase in constellation size and a 6× increase in primary model parameters, the median latency of Polaris 2.0 has not increased significantly because of inference optimizations and significant safety improvements across the systems.

Polaris 2.0 is designed for real-time patient-facing healthcare conversations. Given the large constellation size of over 3 trillion parameters, the architecture was designed to reduce end-to-end latency by allowing the support models to run concurrently with the primary conversational model. Additionally, the median latency is lower because not all the support models are invoked for every user utterance. Given the large size of the LLMs, both open-source and proprietary use-case specific solutions are leveraged to perform inference optimizations, including, for example, FP8-quantized KV cache, continuous batching, paged attention, tensor parallelism, FlashInfer kernels, etc. Further, for individual LLMs, AutoFP8 may be used for both weight and activation quantization by using samples from the training data of the corresponding model for calibration. Use-case specific caching with cache warming, prefix caching and routing reduce the variance of the system latency under load as multiple simultaneous conversations on related use-cases are able to share the KV cache.

Lab/Medication Interactions. LLMs focus on statistical frequency which means corner cases can get ignored. Specific medications sometimes alter lab values (e.g., Farxiga increases glucose in urine) and requires differential lab value analysis.

Lab Reference Range Identification. LLMs can become confused due to many reference ranges on the internet and lacking any medical grounding. Identifying the correct reference range for a patient's lab value given their age, gender, etc. is essential for accurate lab interpretation and avoiding hallucinations.

Longitudinal Lab Analysis. LLMs tend not to interpret sequences of numbers well. Reviewing lab values over time is critical to understanding if a patient is improving or declining, and essential for chronic care coaching.

Condition-Specific Disallowed OTCs. LLMs tend not to be aware of OTC contra-indications for specific conditions. In many conditions, common over-the-counter medications and supplements can be harmful. Our agent allows providers to specify contra-indicated OTCs and will recognize their usage.

Prescription Adherence. LLMs are susceptible to suggestions. Patients often misstate how much of the medication they should take. The specialist ensures dosage values in the EMR are enforced.

OTC Toxicity. Maximum OTC dosage calculations depend on a number of factors including age, weight, composition (capsule, tablets, liquid, etc.) and strength. Language models are not good at reasoning across these different variables.

Drug Misidentification. Drug names are complicated; patients often struggle to pronounce or recall them. A medically-focused LLM needs to guide the patient through a disambiguation and recognition process.

Condition-Specific Restaurant Menu Recommendation. Many online menus are PDFs that are difficult for the common crawl to parse and do not contain the nutritional information needed for patients with specific conditions when eating out at restaurants. The AI agents described herein takes into account several factors including conditions, lab values, and clinical macronutrient guidance to provide the specific menu dish recommendation.

Hospital & Payor Specific Policies. The LLMs that are trained solely on the internet tend to conflate multiple hospital policies, combining them into one aggregate policy. Policy examples include visitation policies for children which are specific to a hospital and even a ward such as ICU, pediatrics, etc.

Identity Verification. LLMs tend not be able to process numbers well, including dates of birth, however for HIPAA compliance this has to be perfect.

Human Intervention. General purpose LLMs and chatbots are not good at identifying situations that require human intervention. For healthcare applications, it is critical to connect the patient to a human when appropriate.

Furthermore, this disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

Although the present technology disclosed has been described in connection with several implementations, the technology disclosed is not intended to be limited to the specific forms set forth herein. On the contrary, it is intended to cover such alternatives, modifications, and equivalents as can be reasonably included within the scope of the technology disclosed as defined by the appended claims.

Some implementations of the technology disclosed relate to using a Transformer model to provide a multi-turn conversational system. In particular, the technology disclosed proposes a parallel input, parallel output (PIPO) multi-turn conversational system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed multi-turn conversational system is a multilayer perceptron (MLP). In another implementation, the disclosed multi-turn conversational system is a feedforward neural network. In yet another implementation, the disclosed multi-turn conversational system is a fully connected neural network. In a further implementation, the disclosed multi-turn conversational system is a fully convolution neural network. In a yet further implementation, the disclosed multi-turn conversational system is a semantic segmentation neural network. In a yet another further implementation, the disclosed multi-turn conversational system is a generative adversarial network (GAN) (e.g., CycleGAN, StyleGAN, pixelRNN, text-2-image, DiscoGAN, IsGAN). In a yet another implementation, the disclosed multi-turn conversational system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLAMA versions, BERT, SpanBERT, ROBERTa, XLNet, ELECTRA, UniLM, BART, T5, ERNIE (THU), KnowBERT, DeiT-Ti, DeiT-S, DeiT-B, T2T-ViT-14, T2T-VIT-19, T2T-VIT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCIT-S12/16, CMT-S, CMT-B, VOLO-D1, VOLO-D2, VOLO-D3, VOLO-D4, MoCo v3, ACT, TSP, Max-DeepLab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, VITB/16-FRCNN, VIT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed multi-turn conversational system is a convolution neural network (CNN) with a plurality of convolution layers. In another implementation, the disclosed multi-turn conversational system is a recurrent neural network (RNN) such as a long short-term memory network (LSTM), bi-directional LSTM (Bi-LSTM), or a gated recurrent unit (GRU). In yet another implementation, the disclosed multi-turn conversational system includes both a CNN and an RNN.

In yet other implementations, the disclosed multi-turn conversational system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed multi-turn conversational system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed multi-turn conversational system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed multi-turn conversational system can include upsampling layers, downsampling layers, recurrent connections, gates and gated memory units (like an LSTM or GRU), residual blocks, residual connections, highway connections, skip connections, peephole connections, activation functions (e.g., nonlinear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed multi-turn conversational system can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed multi-turn conversational system can be an ensemble of multiple models, in some implementations.

In some implementations, the disclosed multi-turn conversational system can be trained using backpropagation-based gradient update techniques. Example gradient descent techniques that can be used for training the disclosed multi-turn conversational system include stochastic gradient descent, batch gradient descent, and mini-batch gradient descent. Some examples of gradient descent optimization algorithms that can be used to train the disclosed multi-turn conversational system are Momentum, Nesterov accelerated gradient, Adagrad, Adadelta, RMSprop, Adam, AdaMax, Nadam, and AMSGrad.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks.

The invention claimed is:

1. A method, comprising:

initiating, by a conversational artificial intelligence executed by one or more processors, a conversation with a human;

receiving, by the conversational artificial intelligence, a human response from the human;

augmenting, by the one or more processors, the human response to create an augmented response;

determining, by the one or more processors, a context of the conversation;

providing, by the one or more processors, the context of the conversation and the augmented response to a plurality of automatic speech recognition (ASR) modules that individually process the augmented response in parallel;

receiving, by the one or more processors, a plurality of intermediate text outputs from the plurality of ASR modules, wherein individual intermediate text outputs of the plurality of intermediate text outputs are received from individual modules of the plurality of ASR modules;

performing in real-time, by a reconciliation artificial intelligence, a contextual reconciliation of the plurality of intermediate text outputs based at least in part on the context of the conversation and on a medical history of the human to create a final text output; and generating, by the conversational artificial intelligence, an artificial intelligence response to the human based at least in part on the final text output.

2. The method of claim 1, wherein augmenting the human response to create the augmented response comprises at least one of:

performing an intonation analysis of the human response;

performing noise cancellation by reducing an amount of background noise present in the human response; or any combination thereof.

3. The method of claim 1, wherein determining the context of the conversation comprises:

accessing electronic medical records (EMR) associated with the human; and determining a conversation history of the conversation between the conversational artificial intelligence and the human.

4. The method of claim 1, wherein the plurality of ASR modules comprise at least:

a first ASR module implemented using a first artificial intelligence algorithm;

a second ASR module implemented using a second artificial intelligence algorithm; and a third ASR module implemented using a third artificial intelligence algorithm;

wherein the first artificial intelligence algorithm, the second artificial intelligence algorithm, and the third artificial intelligence algorithm are different from each other.

5. The method of claim 1, wherein the plurality of ASR modules comprise at least:

a first ASR module trained using a first corpus of speech of people having a first type of accent when speaking a particular language;

a second ASR module trained using a second corpus of speech of people having a second type of accent when speaking the particular language; and a third ASR module trained using a third corpus of speech of people having a third type of accent when speaking the particular language;

wherein the first type of accent, the second type of accent, and the third type of accent are different from each other.

6. The method of claim 1, wherein the conversational artificial intelligence is trained using multi-turn reinforcement learning through human feedback (RLHF).

7. The method of claim 1, wherein the conversational artificial intelligence, during the conversation with the human:

identifies a turn-yielding cue;

performs interruption detection to detect when the human is attempting to interrupt the conversationa; artificial intelligence;

identifies a non-verbal cue associated with the human; or any combination thereof.

8. A server comprising:

one or more processors; and one or more computer-readable storage media to store instructions executable by the one or more processors to perform operations comprising:

initiating, by a conversational artificial intelligence, a conversation with a human;

receiving, by the conversational artificial intelligence, a human response from the human;

augmenting the human response to create an augmented response;

determining a context of the conversation;

providing the context of the conversation and the augmented response to a plurality of automatic speech recognition (ASR) modules that individually process the augmented response in parallel;

receiving a plurality of intermediate text outputs from the plurality of ASR modules, wherein individual intermediate text outputs of the plurality of intermediate text outputs are received from individual modules of the plurality of ASR modules;

performing in real-time, by a reconciliation artificial intelligence, a contextual reconciliation of the plurality of intermediate text outputs based at least in part on the context of the conversation and on a medical history of the human to create a final text output; and generating, by the conversational artificial intelligence, an artificial intelligence response to the human based at least in part on the final text output.

9. The server of claim 8, wherein augmenting the human response to create the augmented response comprises at least one of:

performing an intonation analysis of the human response including determining a volume, a pitch, and a rhythm of individual words in the human response;

performing noise cancellation by identifying speech content spoken by the human and reducing the volume of other content in the human response including other human speech; or any combination thereof.

10. The server of claim 8, wherein determining the context of the conversation comprises:

determining electronic medical records (EMR) associated with the human; and determining a conversation history of the conversation between the conversational artificial intelligence and the human.

11. The server of claim 10, wherein the conversation history of the conversation between the conversational artificial intelligence and the human is stored in a cache memory.

12. The server of claim 8, wherein the plurality of ASR modules comprise at least:

a first ASR module implemented using a first artificial intelligence algorithm;

a second ASR module implemented using a second artificial intelligence algorithm; and a third ASR module implemented using a third artificial intelligence algorithm;

wherein the first artificial intelligence algorithm, the second artificial intelligence algorithm, and the third artificial intelligence algorithm are different from each other.

13. The server of claim 8, wherein the plurality of ASR modules comprise at least:

a first ASR module trained using a first corpus of speech of people having a first type of accent when speaking a particular language;

a second ASR module trained using a second corpus of speech of people having a second type of accent when speaking the particular language; and a third ASR module trained using a third corpus of speech of people having a third type of accent when speaking the particular language;

wherein the first type of accent, the second type of accent, and the third type of accent are different from each other.

14. The server of claim 8, wherein the conversational artificial intelligence is configured to perform specialized healthcare-related functions comprising one or more of:

gathering data related to performing Healthcare Effectiveness Data and Information Set (HEDIS) calculations;

performing a Health Records Assessment (HRA);

determining a Risk Adjustment Factor (RAF);

reviewing a pre-op checklist;

reviewing a discharge checklist;

reviewing a chronic care checklist;

determining social determinants of health (SDOH); or any combination thereof.

15. A non-transitory memory device to store instructions executable by one or more processors to perform operations comprising:

initiating, by a conversational artificial intelligence, a conversation with a human;

receiving, by the conversational artificial intelligence, a human response from the human;

augmenting the human response to create an augmented response;

determining a context of the conversation;

providing the context of the conversation and the augmented response to a plurality of automatic speech recognition (ASR) modules that individually process the augmented response in parallel;

receiving a plurality of intermediate text outputs from the plurality of ASR modules, wherein individual intermediate text outputs of the plurality of intermediate text outputs are received from individual modules of the plurality of ASR modules;

performing in real-time, by a reconciliation artificial intelligence, a contextual reconciliation of the plurality of intermediate text outputs based at least in part on the context of the conversation and on a medical history of the patient to create a final text output; and generating, by the conversational artificial intelligence, an artificial intelligence response to the human based at least in part on the final text output.

16. The non-transitory memory device of claim 15, wherein augmenting the human response to create the augmented response comprises at least one of:

performing an intonation analysis of the human response including determining a volume, a pitch, and a rhythm of individual words in the human response;

performing noise cancellation by identifying speech content spoken by the human and reducing the volume of other content in the human response including other human speech; or any combination thereof.

17. The non-transitory memory device of claim 15, wherein determining the context of the conversation comprises:

determining electronic medical records (EMR) associated with the human; and determining a conversation history of the conversation between the conversational artificial intelligence and the human.

18. The non-transitory memory device of claim 15, wherein the plurality of ASR modules comprise at least:

a first ASR module implemented using a first artificial intelligence algorithm;

a second ASR module implemented using a second artificial intelligence algorithm; and a third ASR module implemented using a third artificial intelligence algorithm;

wherein the first artificial intelligence algorithm, the second artificial intelligence algorithm, and the third artificial intelligence algorithm are different from each other.

19. The non-transitory memory device of claim 15, wherein the plurality of ASR modules comprise at least:

a first ASR module trained using a first corpus of speech of people having a first type of accent when speaking a particular language;

a second ASR module trained using a second corpus of speech of people having a second type of accent when speaking the particular language; and a third ASR module trained using a third corpus of speech of people having a third type of accent when speaking the particular language;

wherein the first type of accent, the type of second accent, and the third type of accent are different from each other.

20. The non-transitory memory device of claim 15, wherein the conversational artificial intelligence is engaged in a task that includes one or more of:

performing a preventative screening;

an intake-related task;

a scheduling-related task;

a pre-op related task;

a discharge-related task;

a chronic care related task; or any combination thereof.

\* \* \* \* \*